US009944894B2

(12) United States Patent
Davis et al.

(10) Patent No.: US 9,944,894 B2
(45) Date of Patent: Apr. 17, 2018

(54) PLURIPOTENT STEM CELL EXPANSION AND PASSAGE USING A ROCKING PLATFORM BIOREACTOR

(71) Applicant: General Electric Company, Schenectady, NY (US)

(72) Inventors: Brian Michael Davis, Albany, NY (US); Kenneth Roger Conway, Clifton Park, NY (US); Evelina Roxana Loghin, Rexford, NY (US); Xiaohua Zhang, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/956,408

(22) Filed: Dec. 2, 2015

(65) Prior Publication Data

US 2016/0340633 A1 Nov. 24, 2016

Related U.S. Application Data

(60) Provisional application No. 62/104,116, filed on Jan. 16, 2015.

(51) Int. Cl.

| C12N 5/00 | (2006.01) |
|---|---|
| C12M 1/00 | (2006.01) |
| C12M 3/06 | (2006.01) |
| C12M 1/26 | (2006.01) |
| C12M 1/33 | (2006.01) |
| C12M 1/36 | (2006.01) |
| C12N 5/0735 | (2010.01) |
| C12N 5/074 | (2010.01) |

(52) U.S. Cl.
CPC ............ *C12M 29/10* (2013.01); *C12M 27/16* (2013.01); *C12M 33/14* (2013.01); *C12M 33/22* (2013.01); *C12M 41/48* (2013.01); *C12M 45/02* (2013.01); *C12M 47/00* (2013.01); *C12M 47/02* (2013.01); *C12N 5/0606* (2013.01); *C12N 5/0607* (2013.01)

(58) Field of Classification Search
CPC ...... C12M 47/00; C12M 29/10; C12M 27/16; C12M 41/48; C12M 47/02; C12M 33/14; C12M 45/02; C12M 33/22; C12N 5/0607; C12N 5/0606

See application file for complete search history.

(56) References Cited

U.S. PATENT DOCUMENTS

| 5,320,963 | A | * | 6/1994 | Knaack | ............ | B01D 21/0018 |
|---|---|---|---|---|---|---|
| | | | | | | 210/615 |
| 6,190,913 | B1 | | 2/2001 | Singh | | |
| 6,544,788 | B2 | | 4/2003 | Singh | | |
| 8,445,273 | B2 | | 5/2013 | Green et al. | | |
| 8,609,406 | B2 | | 12/2013 | Subramanian et al. | | |
| 9,085,754 | B2 | | 7/2015 | Aberdam et al. | | |
| 9,109,193 | B2 | | 8/2015 | Galliher et al. | | |
| 2010/0124781 | A1 | | 5/2010 | Shelley | | |
| 2010/0136690 | A1 | | 6/2010 | Sundstrom et al. | | |
| 2010/0144033 | A1 | | 6/2010 | Ramkumar et al. | | |
| 2012/0207705 | A1 | | 8/2012 | Kara | | |
| 2012/0225480 | A1 | | 9/2012 | Michal et al. | | |
| 2013/0115695 | A1 | * | 5/2013 | Schulz | ............... | C12N 5/0606 |
| | | | | | | 435/366 |
| 2013/0236961 | A1 | | 9/2013 | Michal et al. | | |
| 2014/0057344 | A1 | * | 2/2014 | Brauner-Sreuther | ............ | B01D 21/0042 |
| | | | | | | 435/289.1 |
| 2014/0099711 | A1 | | 4/2014 | Shimoni et al. | | |
| 2014/0242693 | A1 | | 8/2014 | Fryer et al. | | |

FOREIGN PATENT DOCUMENTS

| EP | 2155857 B1 | 5/2013 |
|---|---|---|
| WO | 2008136729 A1 | 11/2008 |
| WO | 2011117821 A1 | 9/2011 |
| WO | 2012115586 A1 | 8/2012 |
| WO | 2013109520 A1 | 7/2013 |
| WO | 2015102528 A1 | 7/2015 |

OTHER PUBLICATIONS

Serra et al. "Improving expansion of pluripotent human embryonic stem cells in perfused bioreactors through oxygen control."J Biotechnol. Aug. 2, 2010;148(4):208-15.*
Moustafa et al. "Large area micropatterning of cells on polydimethylsiloxane surfaces."J Biol Eng. Oct. 24, 2014;8(1):24.*
Walmman et al. "Biogrid—a microfluidic device for large-scale enzyme-free dissociation of stem cell aggregates."Lab Chip. Oct. 7, 2011;11(19):3241-8.*
Ting et al. "An intermittent rocking platform for integrated expansion and differentiation of human pluripotent stem cells to cardiomyocytes in suspended microcarrier cultures." Stem Cell Res. Sep. 2014 ;13(2):202-13. Epub Jun. 27, 2014.*
Zy et al., "Perfusion Culture of Hematopoietic Cells in a Stirred Tank Bioreactor", Chinese Journal of Biotechnology, vol. No. 21, Issue No. 4, Jul. 2005.
Schroeder et al., "Differentiation and Lineage Selection of Mouse Embryonic Stem Cells in a Stirred Bench Scale Bioreactor with Automated Process Control", Biotechnology and Bioengineering, vol. No. 92, Issue No. 7, pp. 920-933, Sep. 2005.
Choo et al., "High-Level Production of a Monoclonal Antibody in Murine Myeloma Cells by Perfusion Culture Using a Gravity Settler", Biotechnology Progress, vol. No. 23, Issue No. 1, pp. 225-231, Feb. 2007.
Bauwens et al., "Control of Human Embryonic Stem Cell Colony and Aggregate Size Heterogeneity Influences Differentiation Trajectories", Stem Cells, vol. No. 26, Issue No. 9, pp. 2300-2310, Sep. 2008.
Niebruegge et al., "Cardiomyocyte Production in Mass Suspension Culture: Embryonic Stem Cells as a Source for Great Amounts of Functional Cardiomyocytes", Tissue Engineering: Part A, vol. No. 14, Issue No. 10, pp. 1591-1601, 2008.
Niebruegge et al.,"Generation of Human Embryonic Stem Cell-Derived Mesoderm and Cardiac Cells. Using Size-Specified Aggregates in an Oxygen-Controlled Bioreactor", Biotechnology and Bioengineering. vol. No. 102, Issue No. 2, pp. 493-507, Feb. 2009.

(Continued)

*Primary Examiner* — Titilayo Moloye
(74) *Attorney, Agent, or Firm* — Pabitra K. Chakrabarti

(57) ABSTRACT

Provided herein are novel methods for expansion and passaging of cell aggregates comprising stem cells and/or differentiated cells and comprising the use of closed systems on rocking platform bioreactors. The methods of the invention permit closed system serial passage expansion of pluripotent stem cells and/or progeny thereof with associated pluripotency markers and differentiation potential.

20 Claims, 30 Drawing Sheets

(56) References Cited

OTHER PUBLICATIONS

Shen et al., "CFD-Aided Cell Settler Design Optimization and Scale-Up: Effect of Geometric Design and Operational Variables on Separation Performance", Biotechnology Progress, vol. No. 27, Issue No. 5, pp. 1282-1296, Sep.-Oct. 2011.

Kempf et al., "Controlling Expansion and Cardiomyogenic Differentiation of Human Pluripotent Stem Cells in Scalable Suspension Culture", Stem Cell Reports, vol. No. 3, Issue No. 6, pp. 1132-1146, Dec. 9, 2014.

Akerstrom, "Expansion of adherent cells for cell therapy", Biology Education Centre, Uppsala University, and GE Healthcare Department of Cell Technologies, pp. 1-31, 2009.

Rowley et al., "Meeting Lot-Size Challenges of Manufacturing Adherent Cells for Therapy", BioProcess International, Mar. 2012.

Ting et al., "An intermittent rocking platform for integrated expansion and differentiation of human pluripotent stem cells to cardiomyocytes in suspended microcarrier cultures", Stem Cell Research, vol. 13, Issue 2, pp. 202-213, Sep. 2014.

Correia et al., "Combining Hypoxia and Bioreactor Hydrodynamics Boosts Induced Pluripotent Stem Cell Differentiation Towards Cardiomyocytes", Stem Cell Review, vol. 10, Issue 6, pp. 786-801, Dec. 2014.

"Cell expansion", GE Healthcare Lifesciences, downloaded from https://promo.gelifesciences.com/GL/XURI/expansion.html#.VL4A5keUf2k, 2015 on Feb. 10, 2015, 2 Pages.

Lars Wallman et al., "Biogrid—a microfluidic device for large-scale enzyme-free dissociation of stem cell aggregates", The Royal Society of Chemistry 2011, www.rsc.org/loc, 8 Pages.

Stephen Parmley, "Accelerating Stem Cells", Sep. 24, 2015 Biocentury Publications, Inc., 2 Pages.

Vincent C. Chen et al. , "Scalable GMP compliant suspension culture system for human ES cells", Available online at www.sciencedirect.com, Stem Cell Research(2012)8, 388-402.

International Search Report and Written Opinion issued in connection with corresponding PCT Application No. PCT/EP2016/050707, dated Apr. 12, 2016.

Brian Michael Davis et al., U.S. Appl. No. 15/075,211, filed Mar. 21, 2016.

* cited by examiner

- 6 well plate (60cm$^2$)- 2 mL x 6 wells x 4 days= 48 mL, 20 M cells
  - 20 M / 48 mL = 420K per mL

- Nonperfusion Xuri (150 mL scale)- 375 mL medium, 300 M cells
  - 300M / 375 mL = 800K per mL

- Perfusion Xuri (1L scale)- 3 L medium, 3.8B cells
  - 3.8B / 3L = 1.27M per mL

FIG. 10

Fold-expansion results

| Flask size | Average | SD | Best |
|---|---|---|---|
| T25 | 3.5 | 1.8 | 6 |
| T75 | 1.6 | 1.1 | 3.4 | ly in flasks, on microcarriers (150 to 250 microns in diameter) or on macrocarriers (~6 mm in diameter) in bioreactors. The use of suspension culture avoids some of the challenges that occur when culturing pluripotent cells on traditional microcarriers including inefficient seeding and release of cells from carriers, physical separation of microcarriers and cells during harvest, and formation of cell-carrier clumping that can lead to phenotypic changes in the cells. Typically, perfusion is used for suspension cultures in bioreactors.

PLURIPOTENT STEM CELL EXPANSION AND PASSAGE USING A ROCKING PLATFORM BIOREACTOR

CROSS REFERENCE TO RELATED APPLICATIONS

This application is a Non-Provisional and claims priority to U.S. Provisional Application No. 62/104,116 titled "Pluripotent Stem Cell Expansion Using a Rocking Platform" filed Jan. 16, 2015, which is incorporated herein by reference in its entirety.

BACKGROUND

This disclosure relates generally to expansion of cells and/or cell aggregates using a rocking platform.

A need for large scale pluripotent stem cell culture is emerging for applications in pluripotent stem cell banking (e.g., for induced pluripotent stem cells), commercial production of cells (e.g., GE's Cytiva™ cardiomyocytes), and cell expansion for clinical trials. Advances in feeder-free pluripotent stem cell culture have enabled large scale cell expansion in flasks, on microcarriers (150 to 250 microns in diameter) or on macrocarriers (~6 mm in diameter) in bioreactors. The use of suspension culture avoids some of the challenges that occur when culturing pluripotent cells on traditional microcarriers including inefficient seeding and release of cells from carriers, physical separation of microcarriers and cells during harvest, and formation of cell-carrier clumping that can lead to phenotypic changes in the cells. Typically, perfusion is used for suspension cultures in bioreactors.

However one challenge in perfusion/suspension culture is how to retain the cells in the bioreactor. Prior art provides some basic separation techniques—1) filtration, 2) gravity sedimentation, and 3) centrifugation. Filtration methods require some means to keep the filter from clogging over the required weeks of operation. A problem with gravity sedimentation is the varying sedimentation characteristics of different cells, the difficulty in scale-up to industrial systems, and difficulty in maintaining sterility. Similarly, centrifugation is routinely used in open cell culture but has found limited application in fully closed system cell culture due to concerns regarding sterility.

There is a need in the field for techniques which reduce human intervention and cross-contamination during the process of culturing cells, including pluripotent stem cells and/or differentiated human cells.

BRIEF DESCRIPTION

Described herein are improved methods for culturing cells, including pluripotent stem cells and/or differentiated human cells.

Provided herein are methods for expansion of cell aggregates in a closed system comprising
  a cell culture vessel on a rocking platform;
  automated perfusion of cell aggregates in the vessel; and
  membrane-free filtration of cell aggregates during the perfusion.

In another aspect, provided herein is a method for expansion of cell aggregates in a closed system comprising
  a cell culture vessel on a rocking platform bioreactor;
  aggregate formation in the vessel;
  automated perfusion of cell aggregates in the vessel;
  membrane-free filtration of cell aggregates during the perfusion; and
  aggregate harvest and passaging in the closed system.

Further provided herein is a method for passaging cell aggregates wherein cell aggregates are reduced in size by a slicer grid associated with a bioreactor in a closed system.

Also provided herein are closed systems for use in expansion of cell aggregates using the methods described herein.

DRAWINGS

These and other features, aspects, and advantages of the present invention will become better understood when the following detailed description is read with reference to the accompanying drawings in which like characters represent like parts throughout the drawings, wherein.

Figure 1:
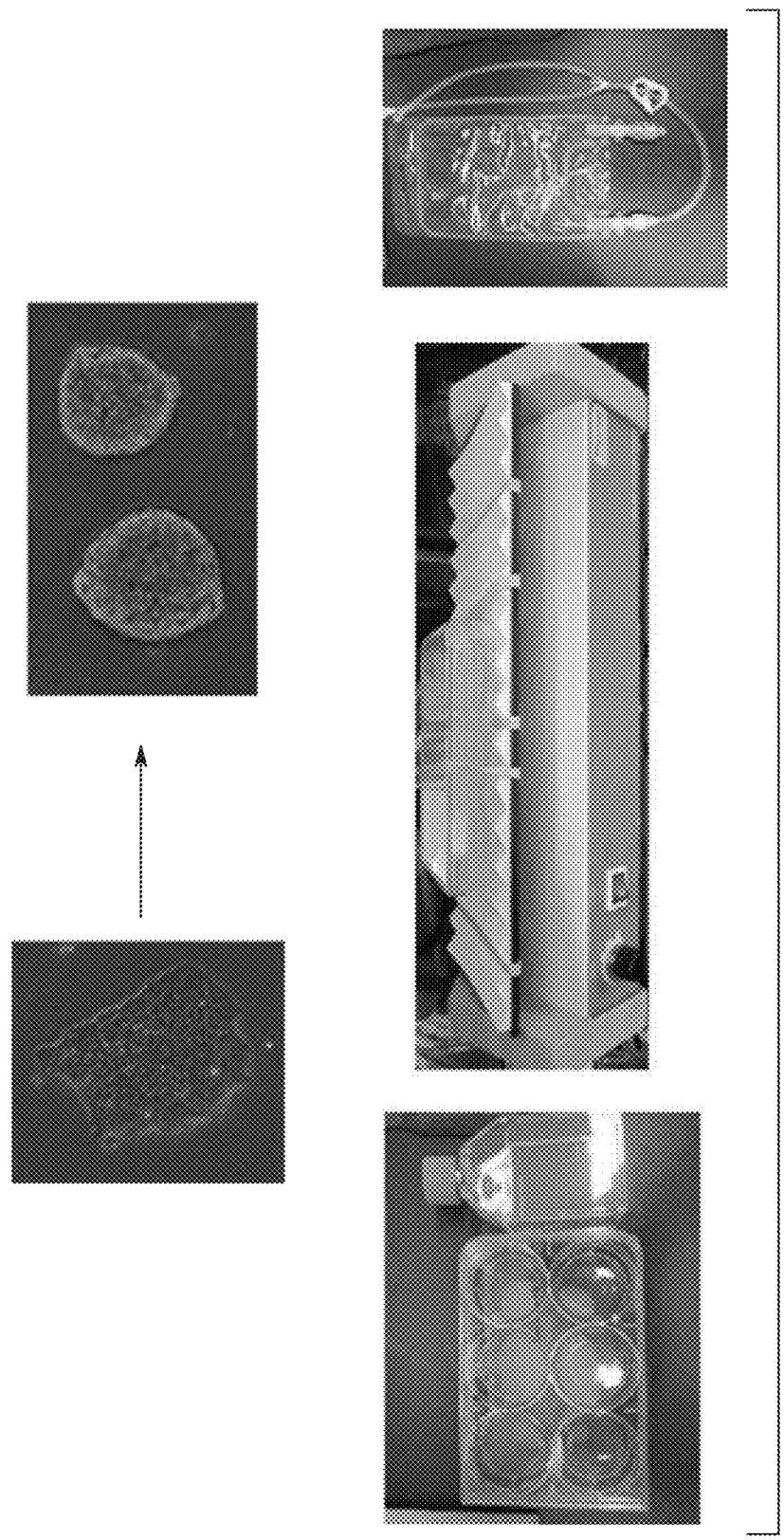
FIG. 1 shows adaptation for expansion greater than 10 passages. Prior to culture in a cell culture vessel (e.g., a Xuri Cellbag bioreactor) the cells are adapted from Matrigel™ to suspension aggregates on low attachment 6 well plates and flasks, or in VueLife bags under rocking conditions.
Figure 2:
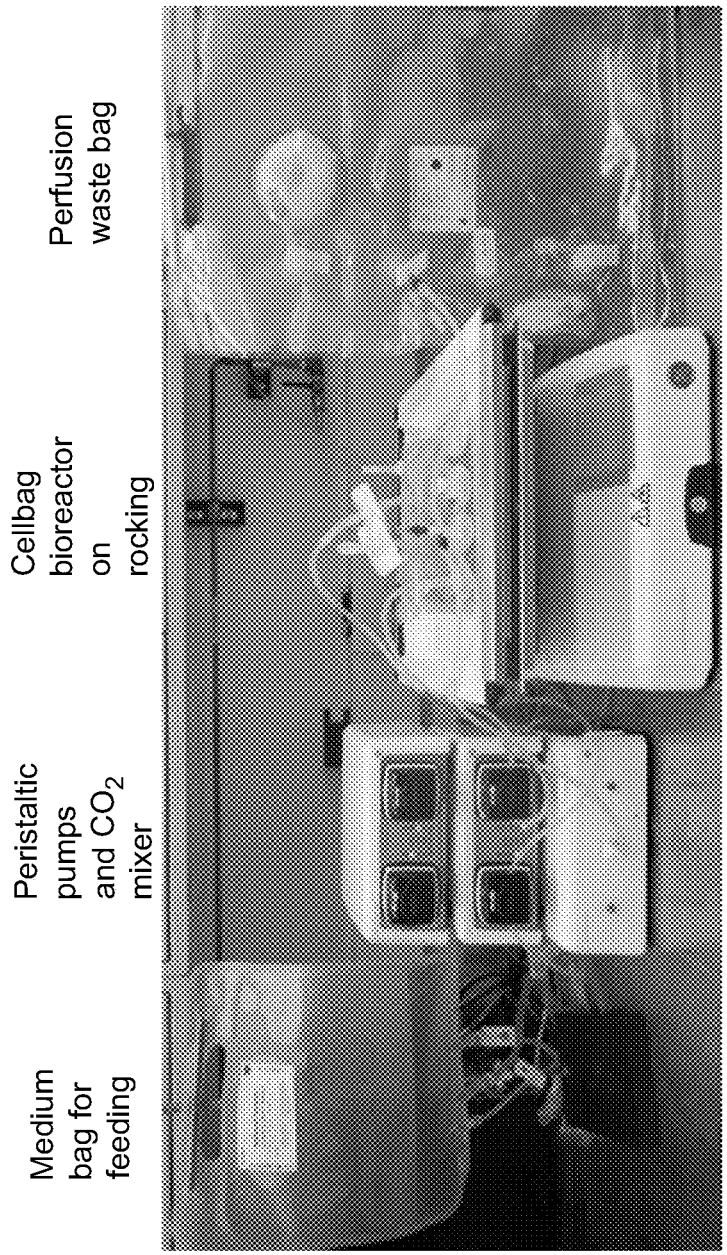
FIG. 2 shows a schematic representation of an exemplary system, i.e., a Xuri W25 system for pluripotent stem cell culture.
Figure 3:
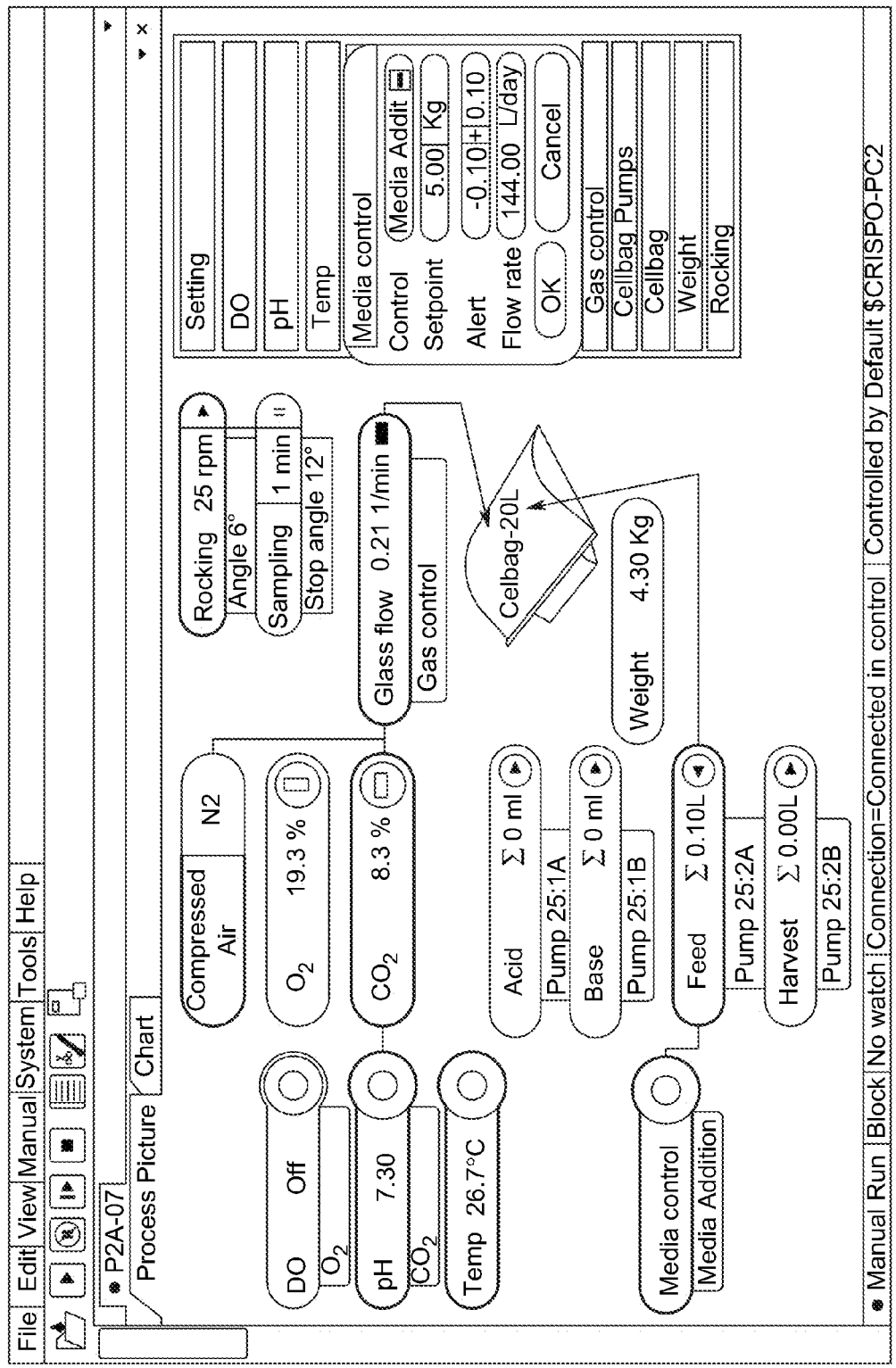
FIG. 3 shows a sample image of a user interface for control software. The sample image shown is not meant to represent and/or otherwise limit the culture conditions described herein.
Figure 4:
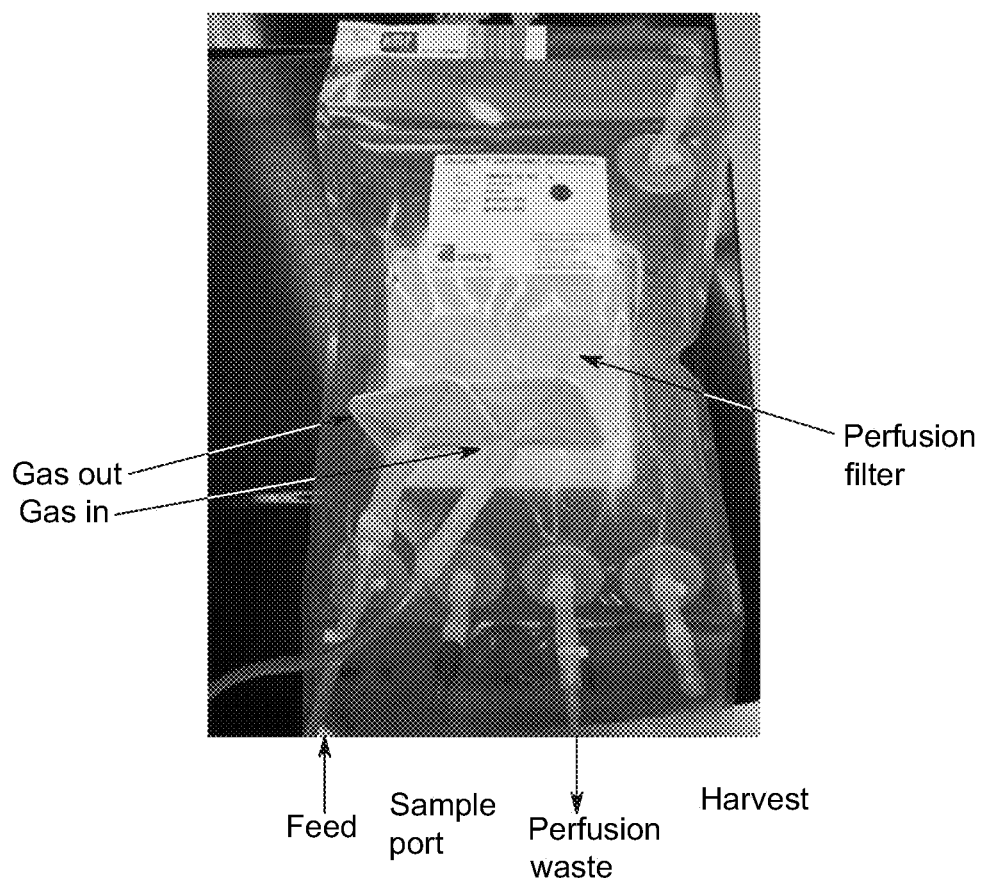
FIG. 4 shows a Xuri Cellbag Bioreactor.
Figure 5:
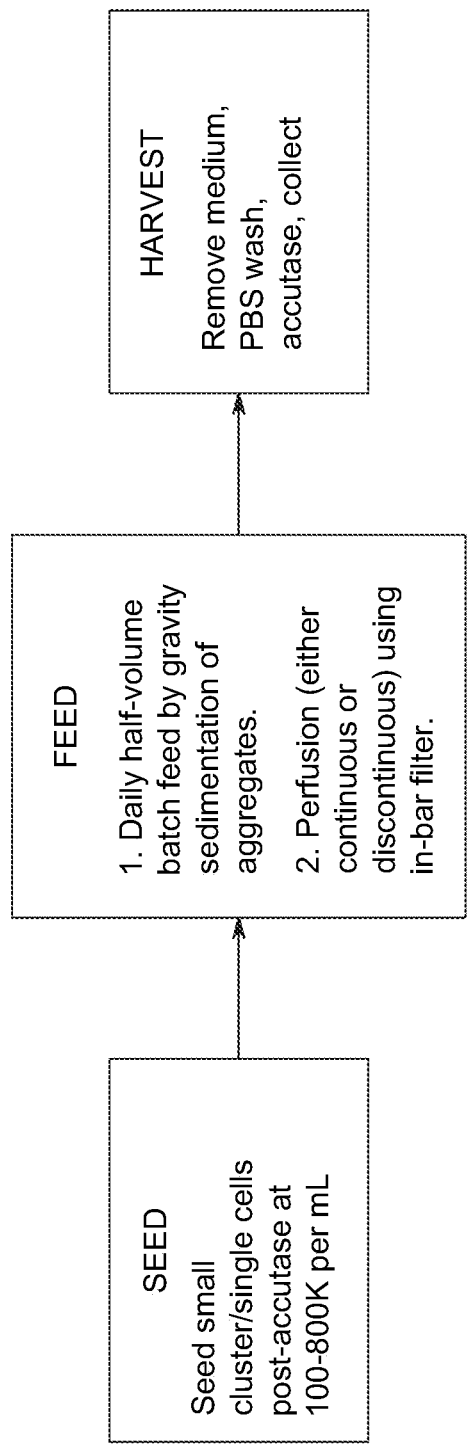
FIG. 5 shows a closed system cell culture process in a Xuri W25 system. All steps were performed on Xuri W25 system in 2 L Cellbag bioreactors using integrated pumps, software controls and load cell.
Figure 6:
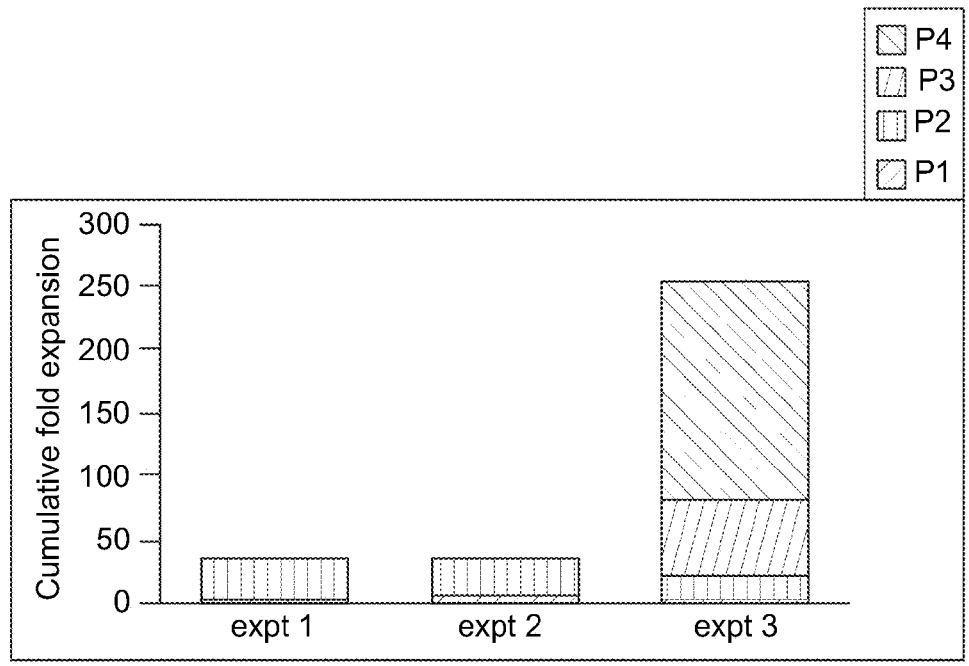
FIG. 6 shows results from expansion in a Xuri W25 system. Higher expansion rates were observed with perfusion cultures.
Figure 7:
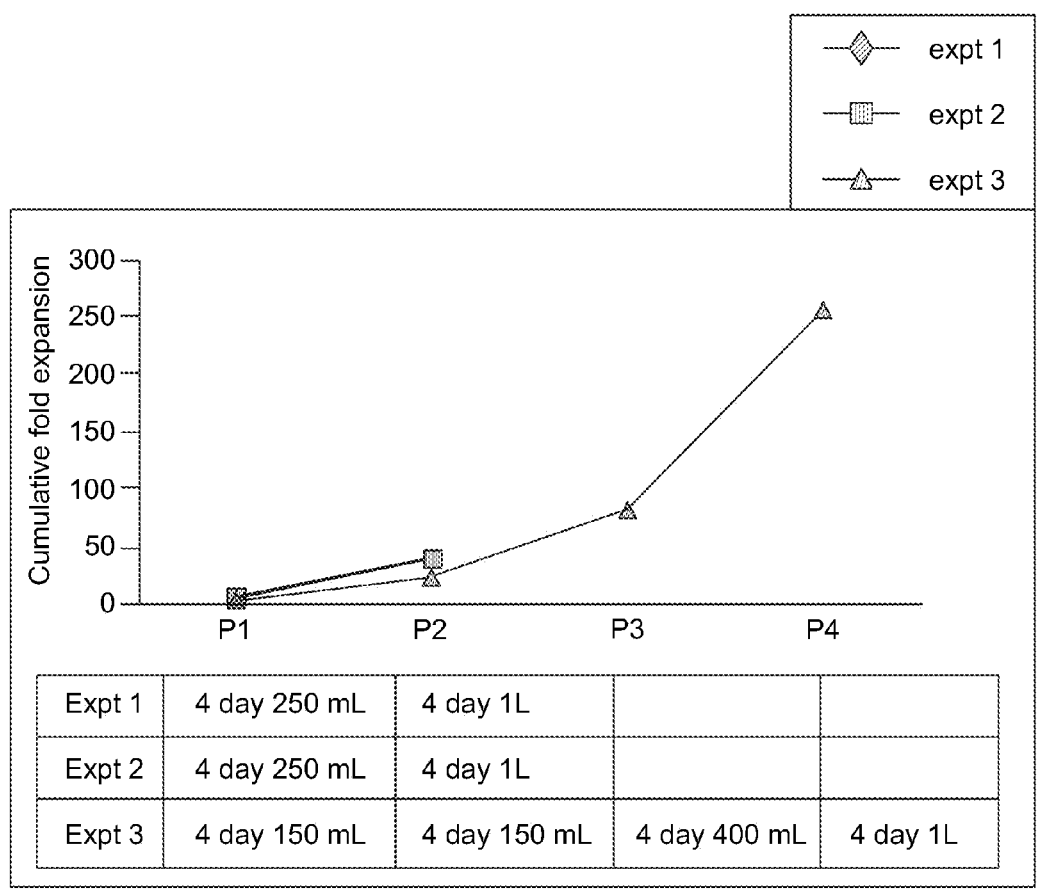
FIG. 7 shows results from expansion in a Xuri W25 system.
Figure 8:
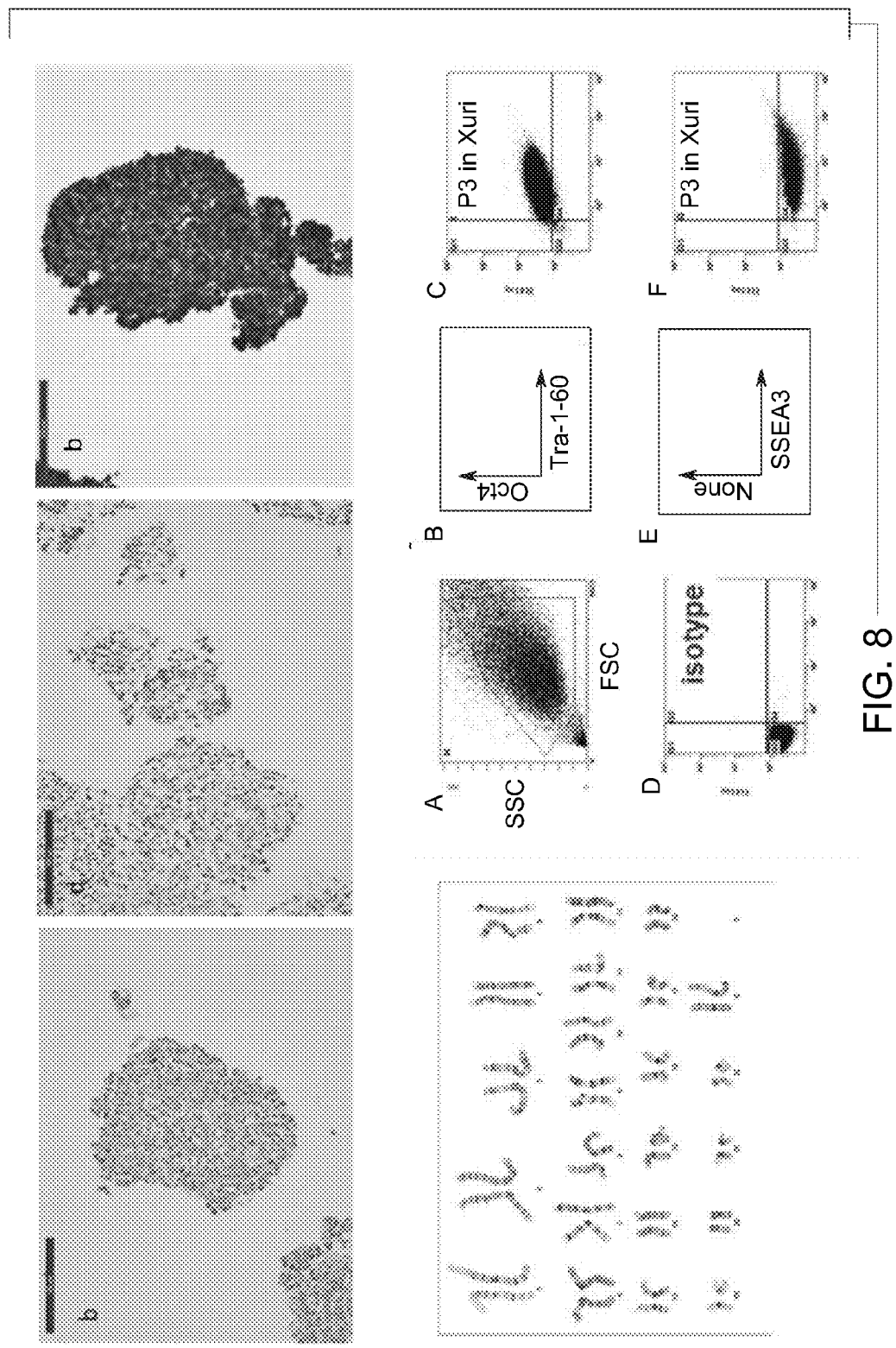

FIG. 8 top row shows the differentiation potential of CT2 human embryonic stem cell aggregates expanded for 5 passages in 6 well plates and 3 passages as suspension aggregates in Xuri Cellbags, confirming the maintenance of pluripotency. FIG. 8 A-F and Example 2 show analysis of pluripotency markers by flow cytometry on CT2 human embryonic stem cell aggregates after five serial passages in 6 well plates and three serial passages in Cellbags. Also shown is the karyotype for CT2 human embryonic stem cell aggregates expanded for 5 passages in 6 well plates and 3 passages as suspension aggregates in Xuri Cellbags.

Figure 9:
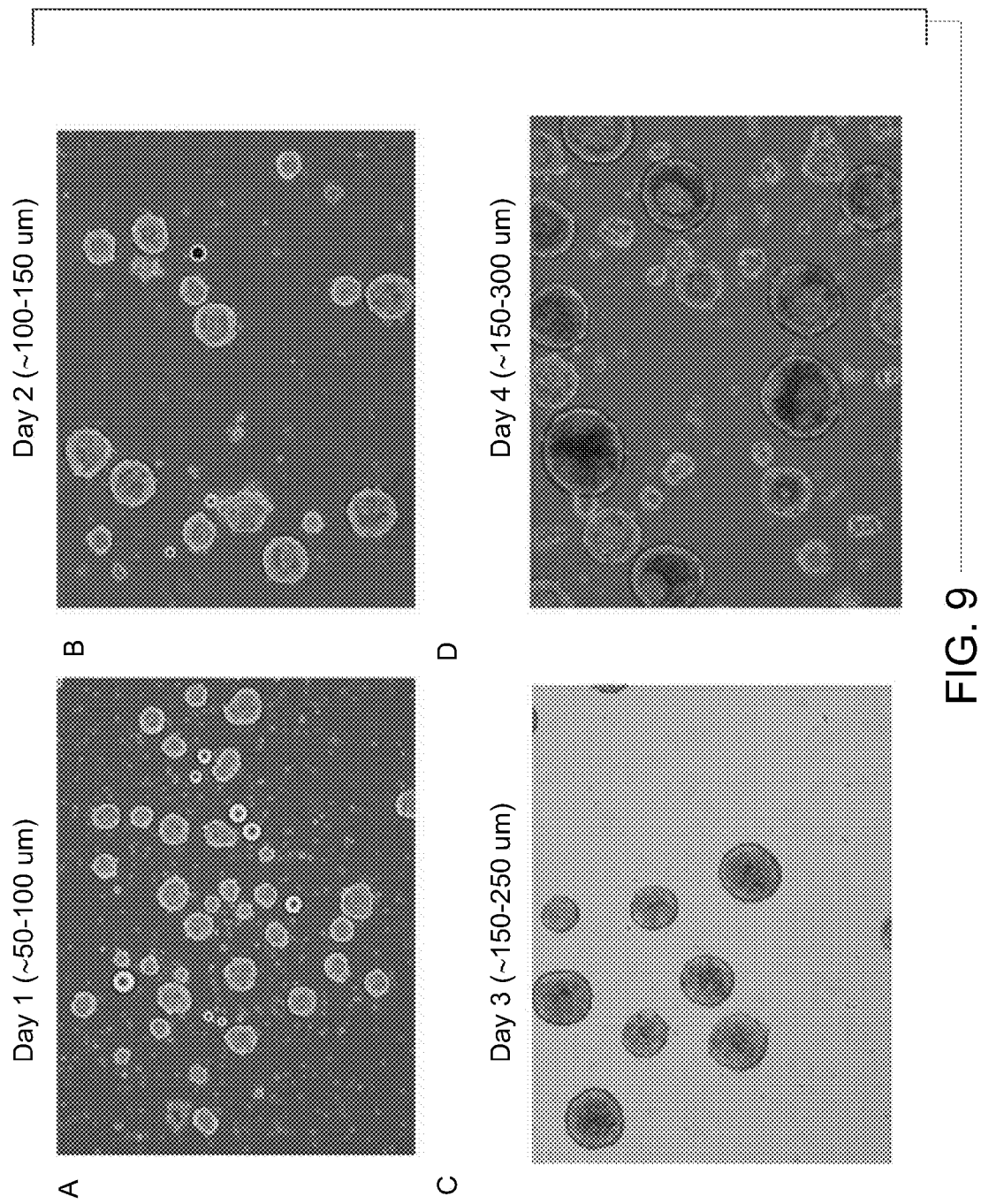

FIG. 9 shows an example of aggregate morphology in Xuri Cellbag bioreactors using the methods described herein.

FIG. 10 shows medium consumption and cell yield over 4 days.

Figure 11:
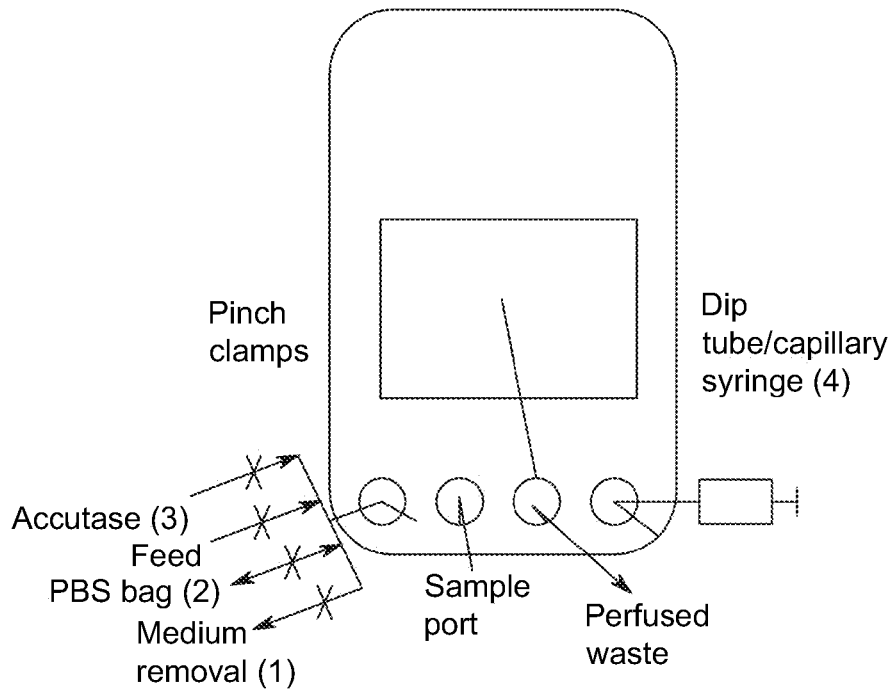

FIG. 11 shows a closed system passage with a perfusion Cellbag. Optional: Remove majority of medium through perfusion filter. Hang bag at angle to allow aggregates to gravity settle in corner. Deflate bag if no dip tube is present. Pull off majority of medium using peristaltic pump. If no dip tube is present, tilt bag backwards to remove most medium. (1). Tube fuse bag with PBS to wash cells. (2). Repeat gravity settling and remove majority of PBS using above process. (2). Tube fuse bag with prewarmed accutase and pump into Cellbag (3). Pinch pellet to resuspend aggregates in Accutase™, incubate 5-8 minutes. Pass Accutased™ cells through capillary or modified syringe to break apart (4). Add medium and harvest dissociated cells, or passage to next bag/culture system (1 or 4).

Figure 12:
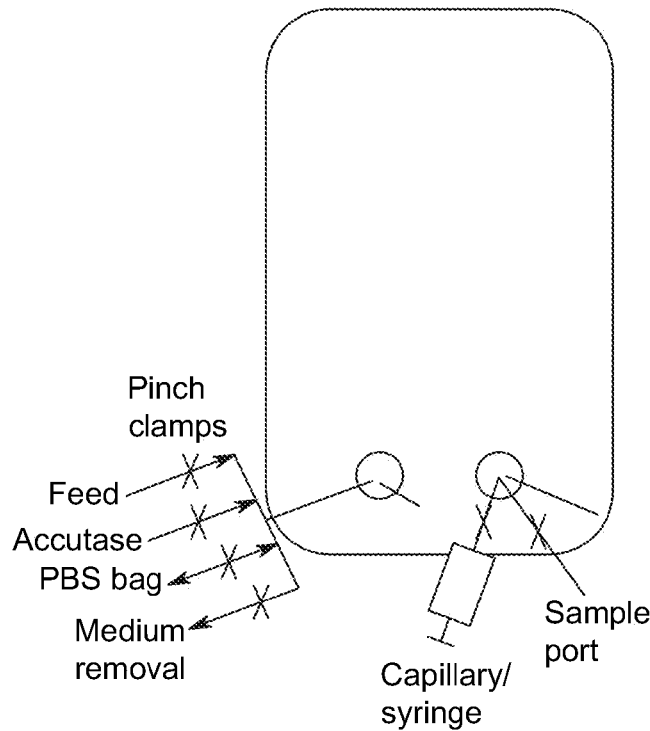

FIG. 12 shows a closed system medium exchange and passage with a non-perfusion Cellbag. For a 50 to 80% medium exchange without dip tube: Hang bag at 60° angle to allow aggregates to gravity settle for 2-5 minutes (depending on aggregate size). For smaller culture volumes, user needs to deflate bag before aggregates settle. Use peristaltic pump to pull off spent medium into waste bag. Pinch seam at bottom of bag to resuspend settled aggregates then begin rocking again. Tube fuse bag with warmed medium onto Cellbag, and use peristaltic pump to add medium while rocking. With dip tube, larger volumes can be removed and bag deflation is not necessary.

Figure 13:
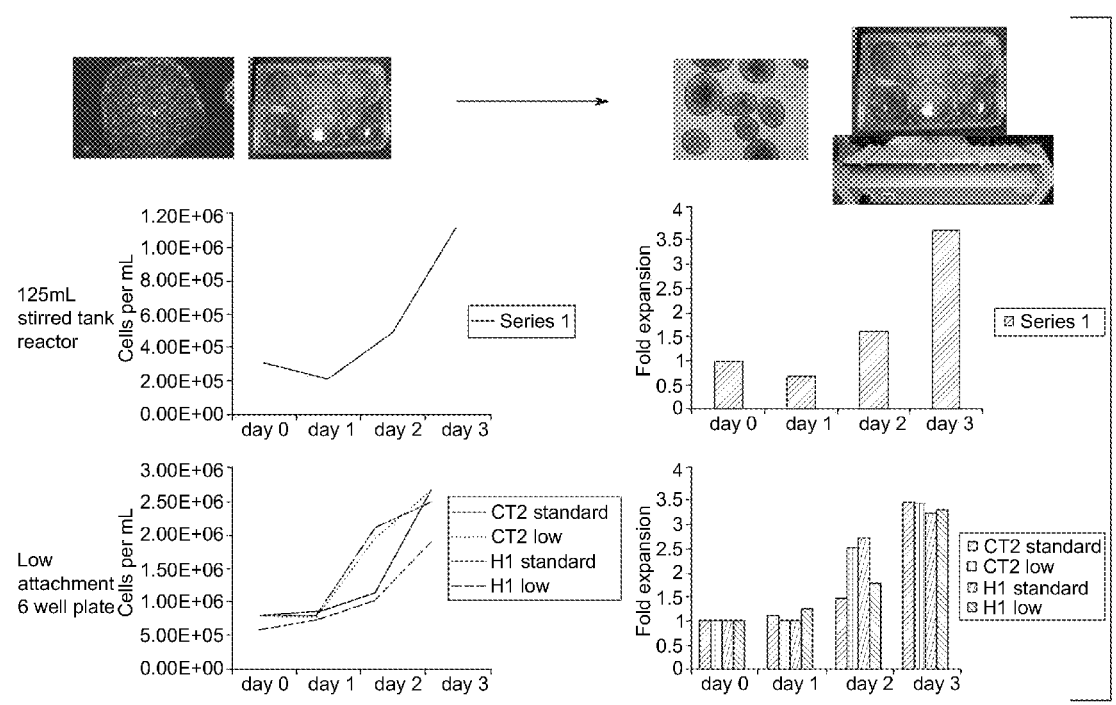
Figure 14:
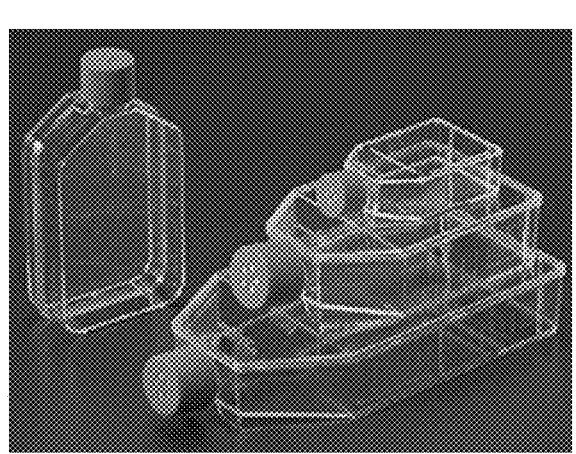

FIG. 13 shows adaptation of adherent cells to suspension cell culture. The methods described herein provided a reproducible process with fold-expansion ranges between 3 to 14-fold over 3-4 days, and >98% viability FIG. 14 shows a sample scale up to larger flasks/vessels. Scale up shown from 2 mL to 10 mL for T25 and 30 mL for T75. Flasks are placed on a rocker to mimic Wave bioreactor motion. The efficiencies of aggregate formation and expansion are reduced as scale increases. It was observed that the length of liquid path at various rock speeds/rock angles influences expansion rates. Accordingly, rocking angle and speed of rocking are adjusted as the scale increases.

Figure 15:
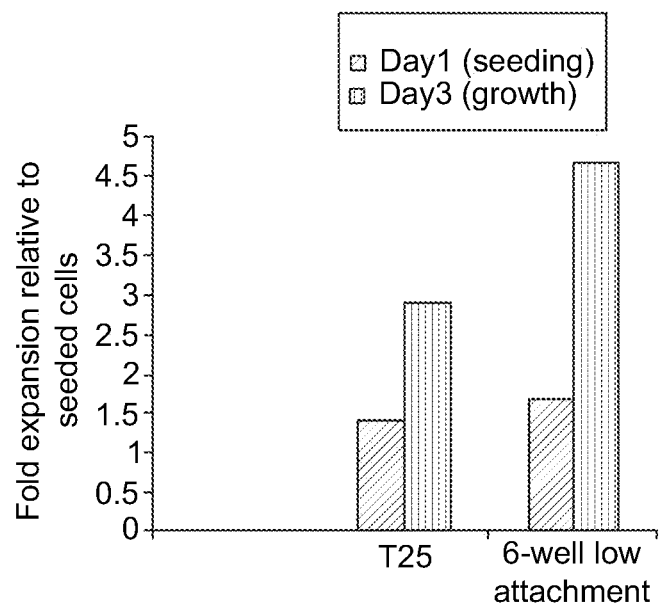
Figure 16:
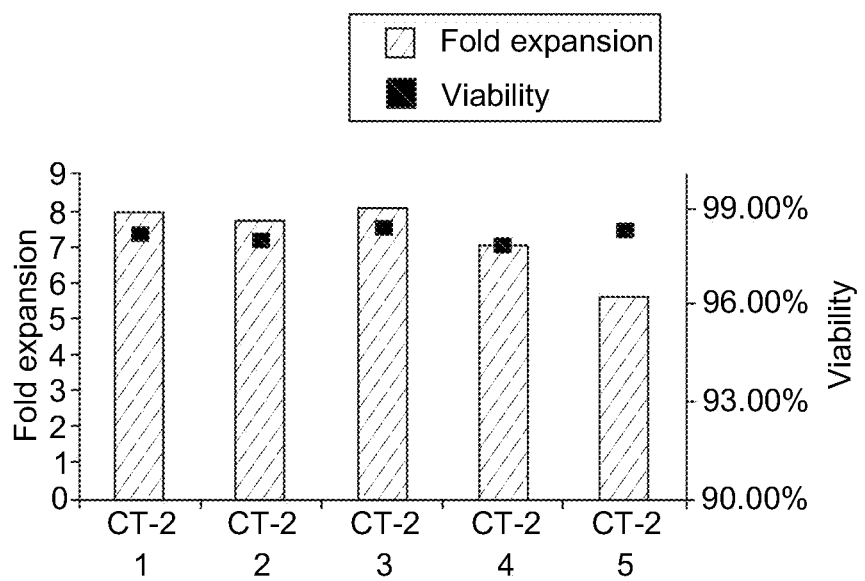

FIG. 15 shows data from expansion and passaging of suspension aggregate pluripotent stem cells in 6 well plates or T flasks FIG. 16 FIG. 16 shows expansion rate comparison after enzymatic passaging or mechanical passaging with the slicer on CT2 human embryonic stem cell aggregates seeded at 4×10^5 cells per mL. (1) CT-2 passaged with Accutase®+ROCK inhibitor; (2) CT-2 passaged with square grid+ROCK inhibitor; (3) CT-2 passaged with hexagon grid+ROCK inhibitor; (4) CT-2 passaged with square grid without ROCK inhibitor; (5) CT-2 passaged with hexagon grid without ROCK inhibitor.

Figure 17:
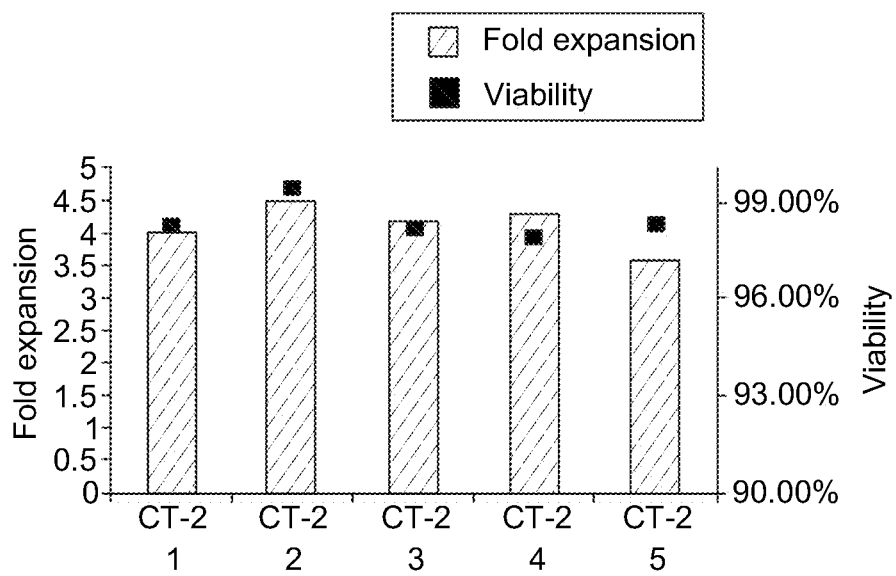

FIG. 17 shows expansion rate comparison after enzymatic passaging or mechanical passaging with the slicer on CT2 human embryonic stem cell aggregates seeded at 1.5×10^6 cells per mL. (1) CT-2 passaged with Accutase®+ROCK inhibitor; (2) CT-2 passaged with square grid+ROCK inhibitor; (3) CT-2 passaged with hexagon grid+ROCK inhibitor; (4) CT-2 passaged with square grid without ROCK inhibitor; (5) CT-2 passaged with hexagon grid without ROCK inhibitor.

Figure 18:
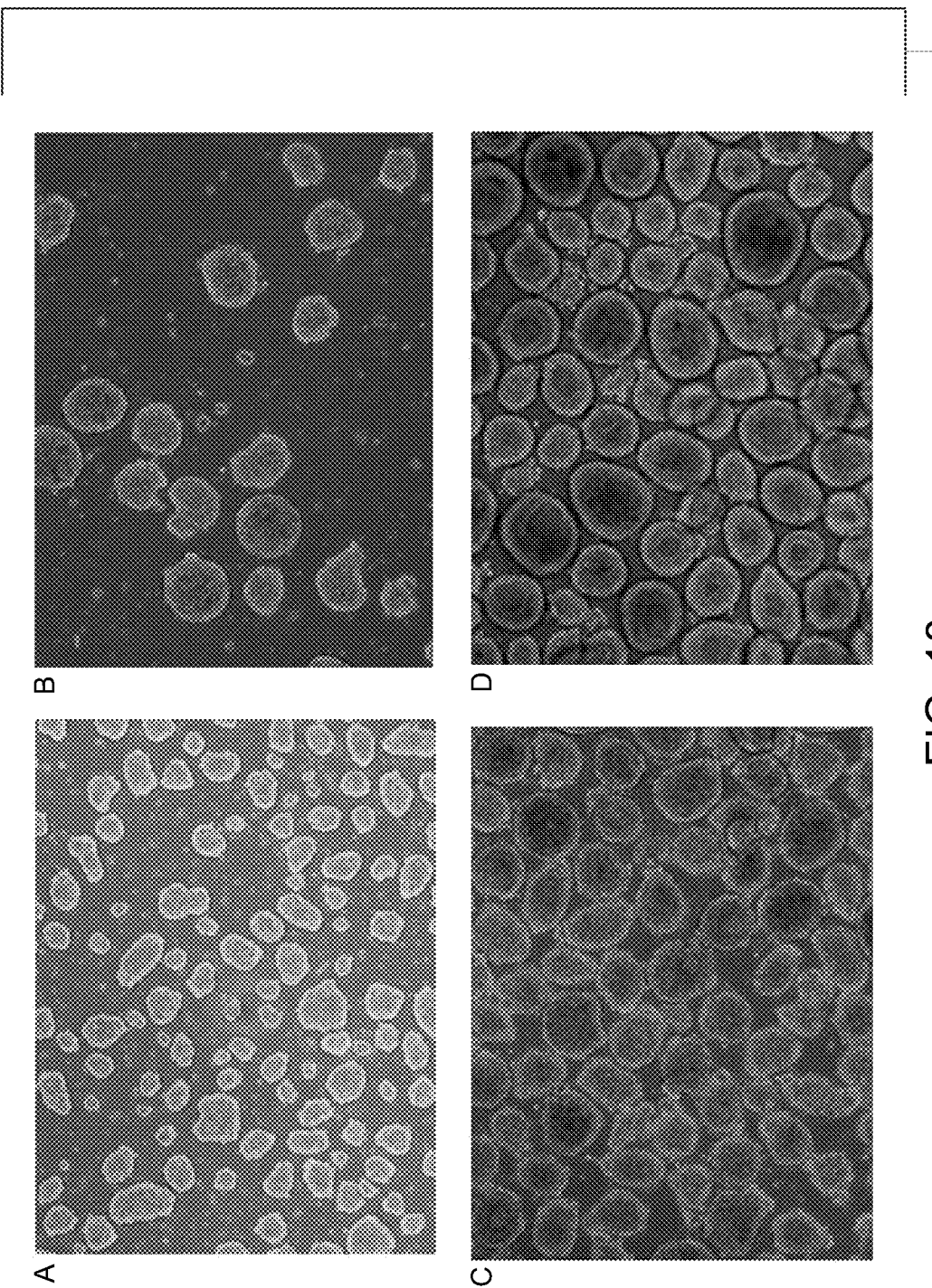

FIG. 18 shows CT2 human embryonic stem cell aggregate morphology after Accutase™ dissociation on A) day 1, B) day 2, C) day 3, and D) day 4.

Figure 19:
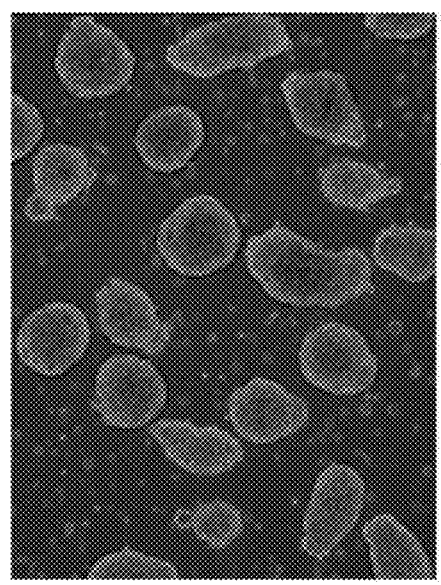
Figure 19:
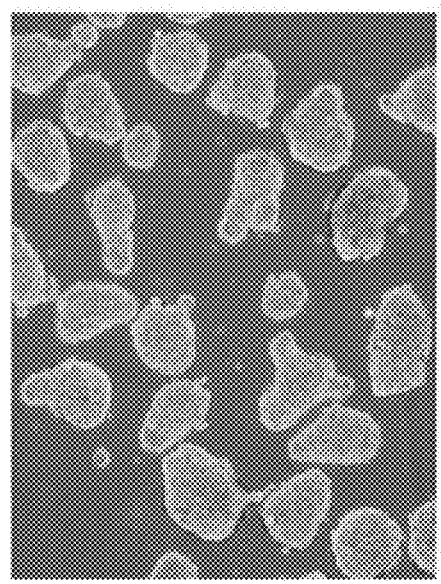
Figure 19:
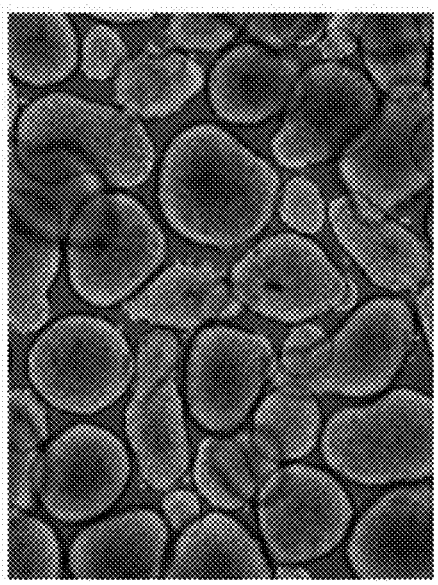

FIG. 19 shows CT2 human embryonic stem cell aggregate morphology after slicing with a square grid slicer on A) day 1, B) day 2, and C) day 4.

Figure 20:
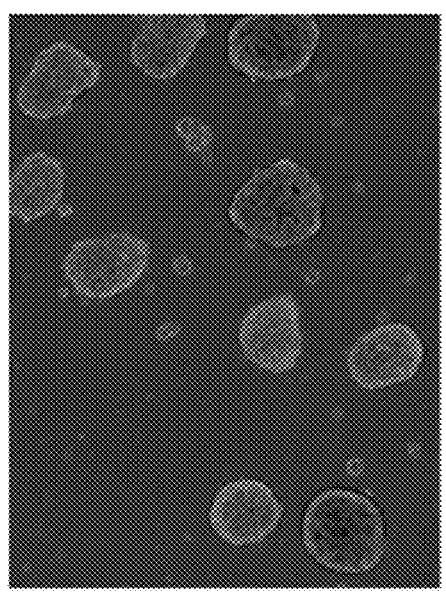
Figure 20:
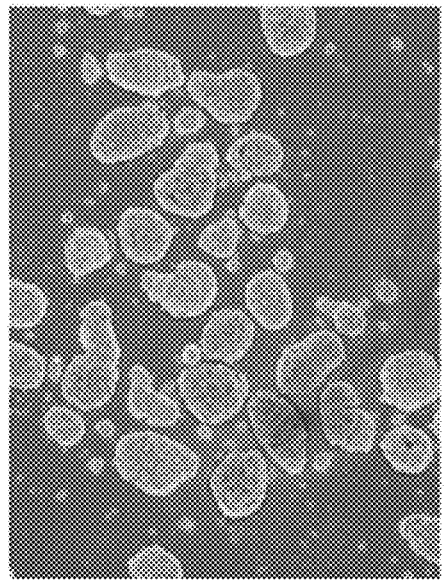
Figure 20:
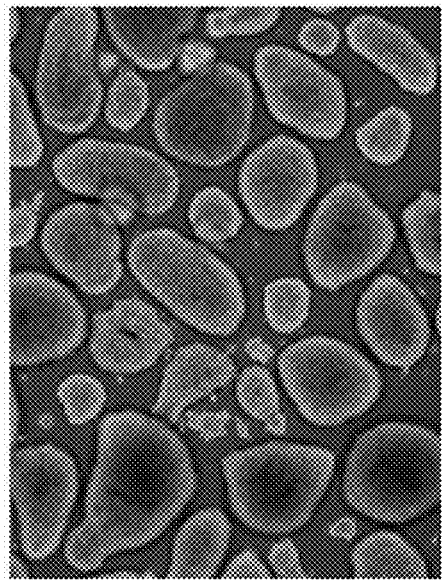

FIG. 20 shows CT2 human embryonic stem cell aggregate morphology after slicing with a hexagonal grid slicer on A) day 1, B) day 2, and C) day 4.

Figure 21:
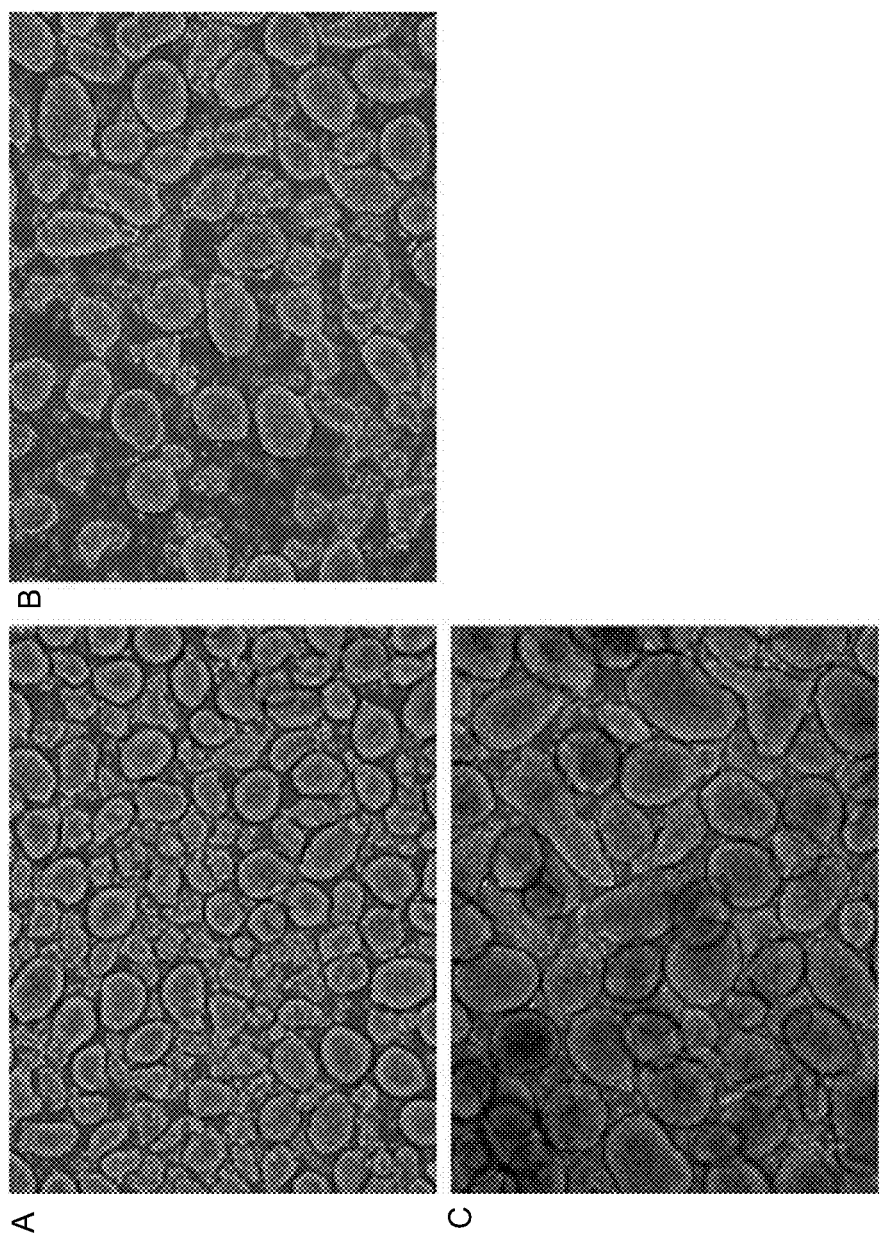

FIG. 21 shows CT2 human embryonic stem cell aggregate morphology after slicing with a hexagonal grid slicer on A) day 1, B) day 2, and C) day 4 when cultured in medium that contains no Y27632 ROCK inhibitor.

Figure 22:
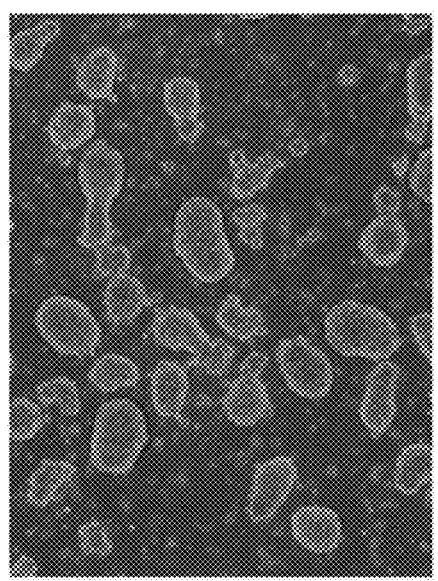
Figure 22:
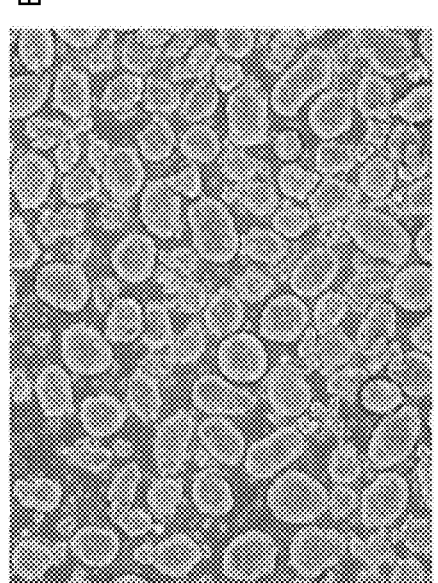
Figure 22:
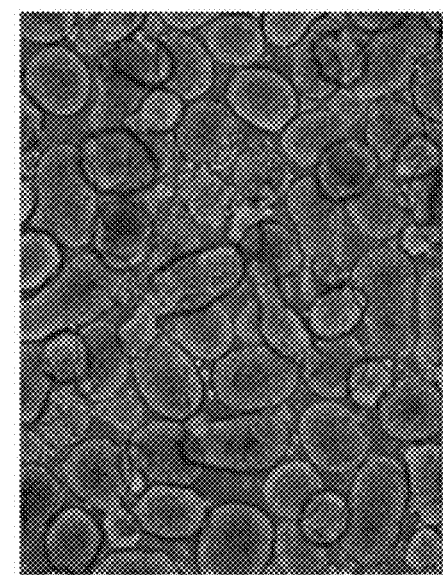

FIG. 22 shows CT2 human embryonic stem cell aggregate morphology after slicing with a square grid slicer on A) day 1, B) day 2, and C) day 4 when cultured in medium that contains no Y27632 ROCK inhibitor.

Figure 23:
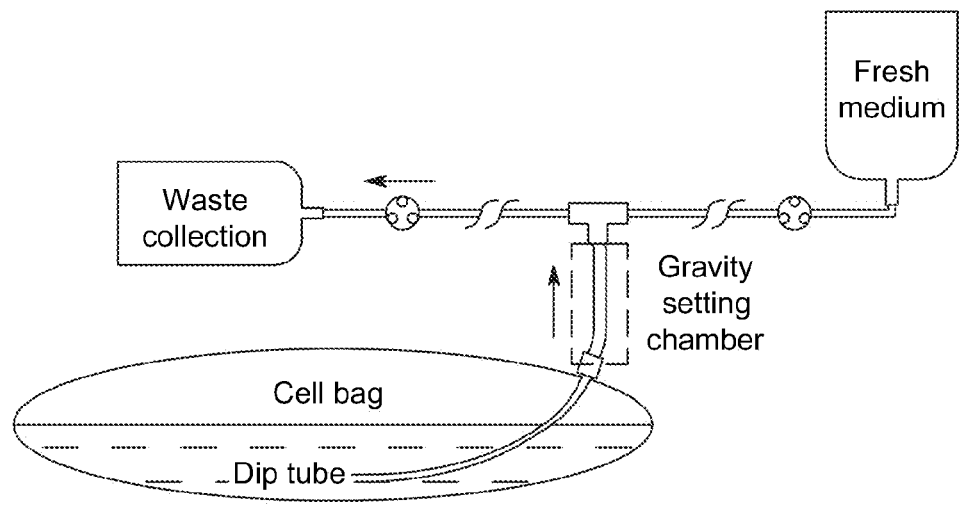

FIG. 23 shows a diagram of the tubing assembly for gravity settling and medium exchange in non-perfusion bags in which spent medium is being removed from the Cellbag.

Figure 24:
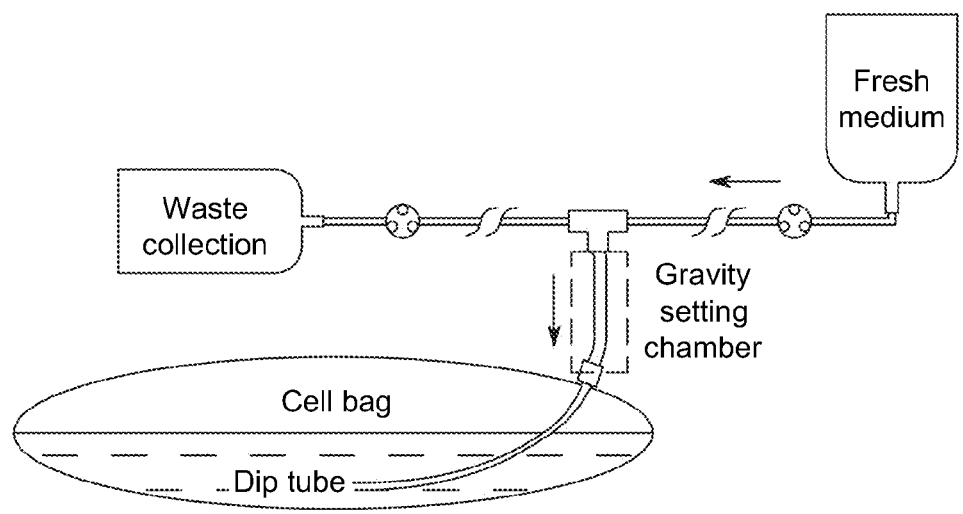

FIG. 24 shows a diagram of the tubing assembly for gravity settling and medium exchange in non-perfusion bags in which fresh medium is being added to the Cellbag.

Figure 25:
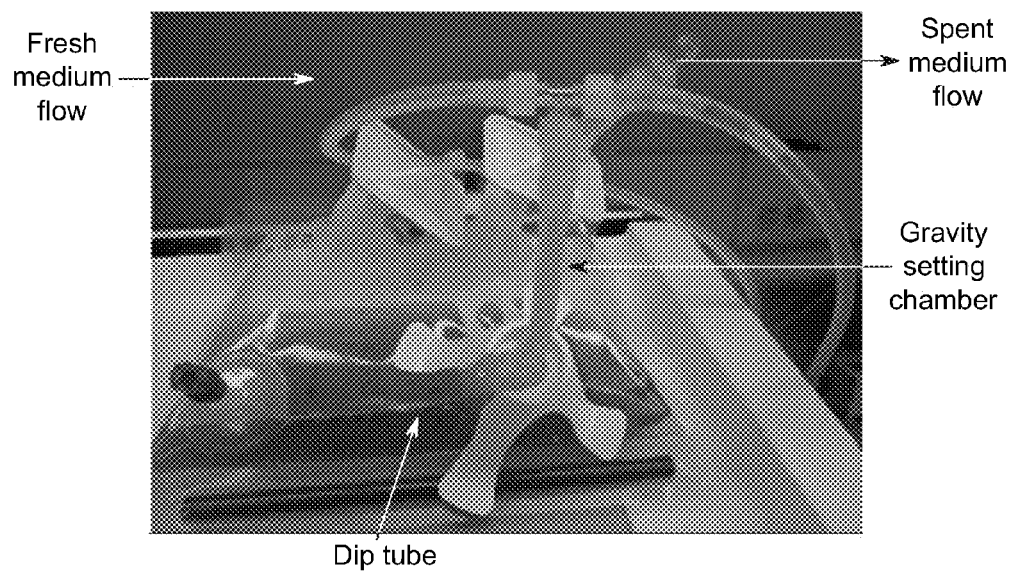

FIG. 25 shows an image of the tubing assembly for gravity settling and medium exchange attached to a non-perfusion Cellbag.

Figure 26:
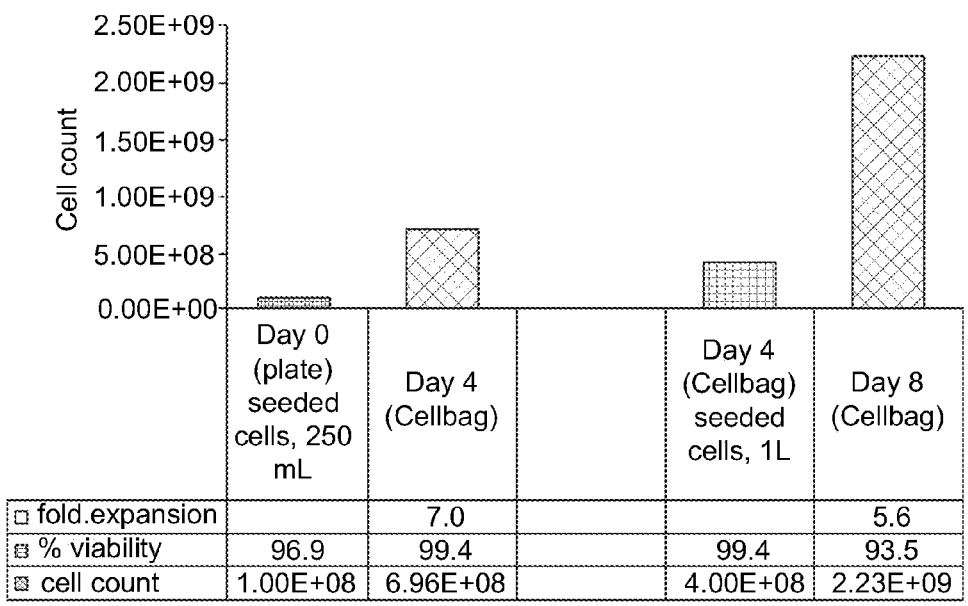

FIG. 26 serial passaging of CT2 human embryonic stem cell aggregates from a filterless non-perfusion Cellbag to a perfusion Cellbag that contains a floating membrane. Serial passaging of CT-2 aggregates was carried out using Accutase® first in 1 L non-perfusion Cellbag at 250 mL volume then in 2 L perfusion Cellbag at 1 L volume.

Figure 27:
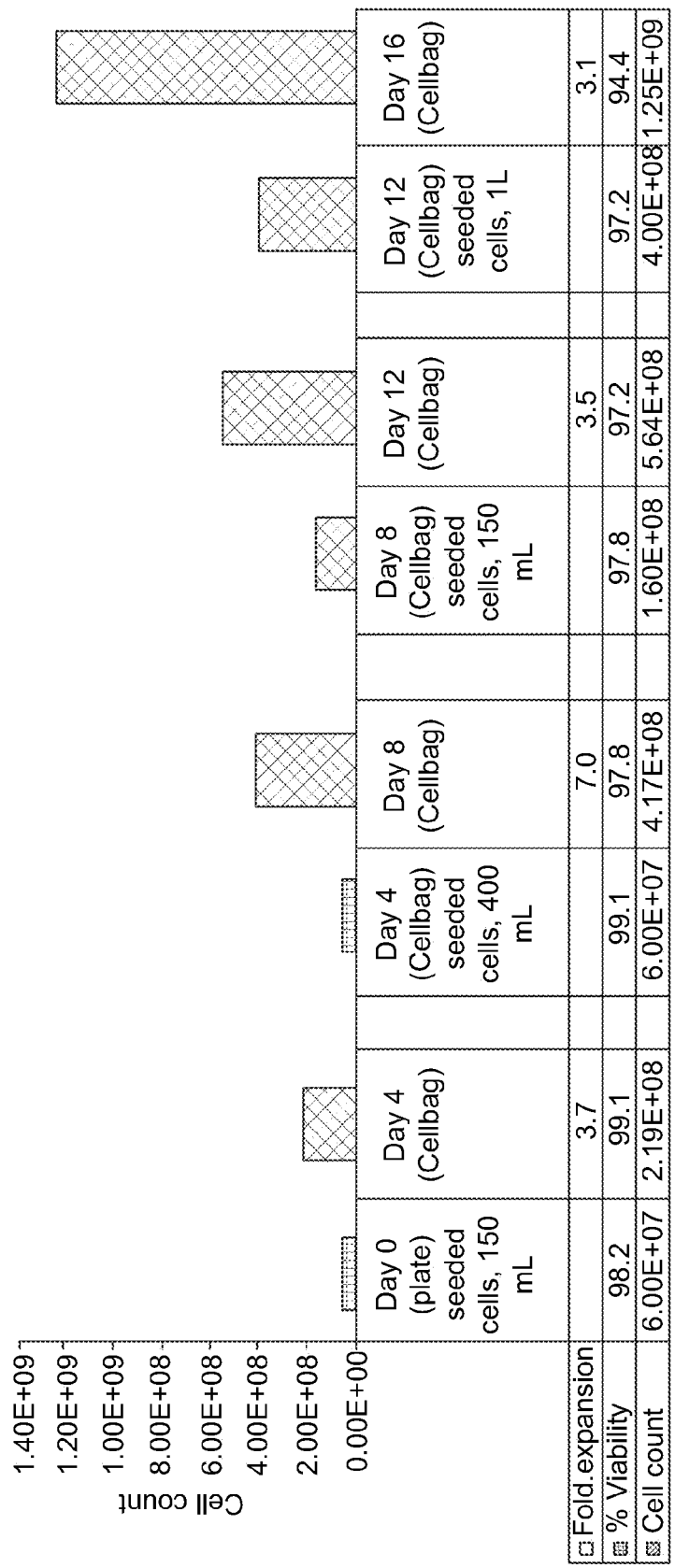
Figure 28:
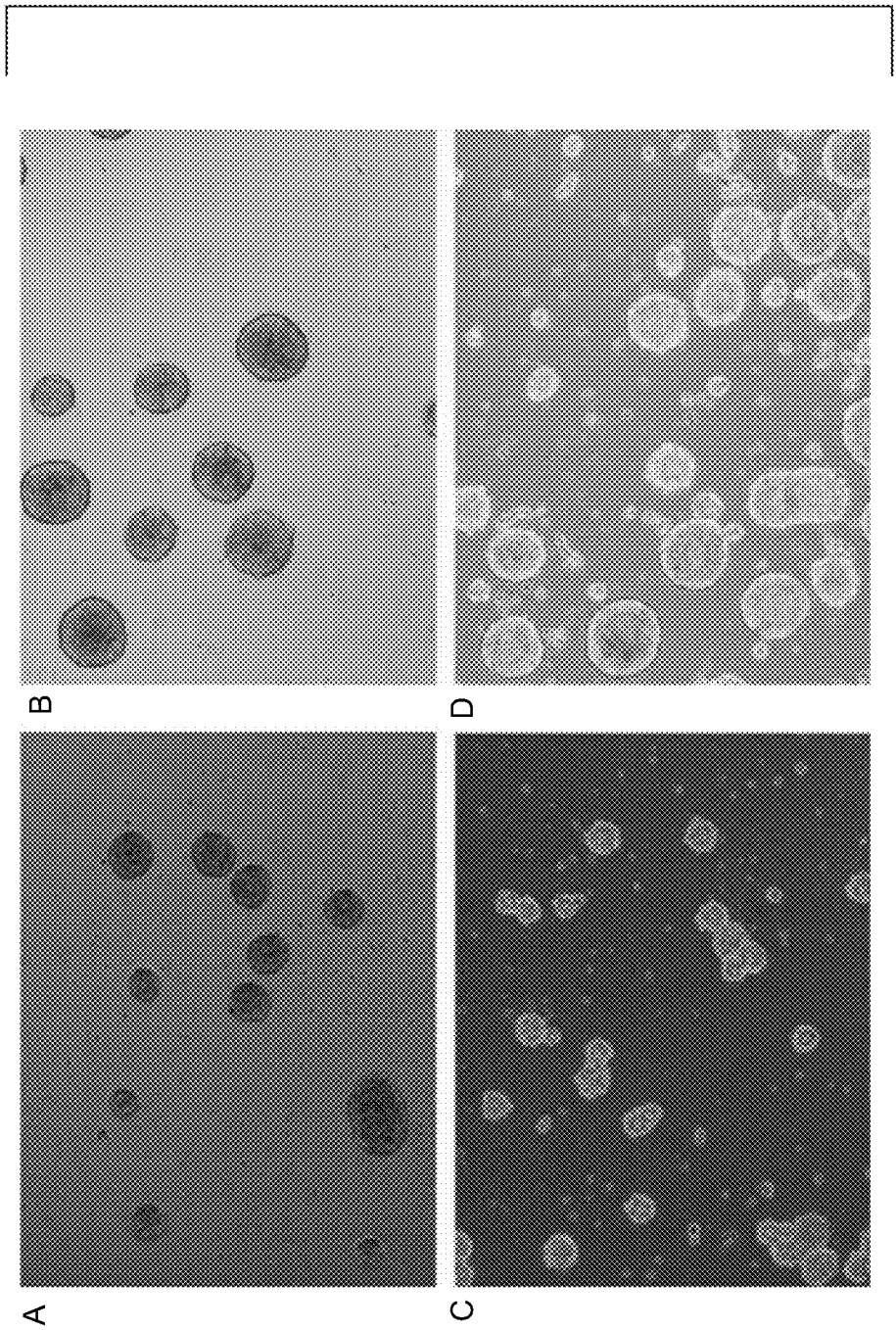

FIG. 27 shows expansion during serial passaging of CT2 human embryonic stem cell aggregates across different volumes and types of Cellbag. Serial passaging of CT-2 aggregates was carried out using Accutase® in 1 L non-perfusion Cellbag at 150 mL volume to 1 L non-perfusion Cellbag at 150 mL volume to 1 L non-perfusion Cellbag at 400 mL volume to 2 L perfusion Cellbag at 1 L volume FIG. 28 shows images of CT2 human embryonic stem cell aggregate morphology during serial passaging in a Cellbag using Accutase™ for enzymatic dissociation and formation of aggregates from dissociated cells in a Cellbag. A) day 1, serial passage 2, B) day 4, serial passage 2, C) day 1 serial passage 3, D) day 4 serial passage 3.

Figure 29:
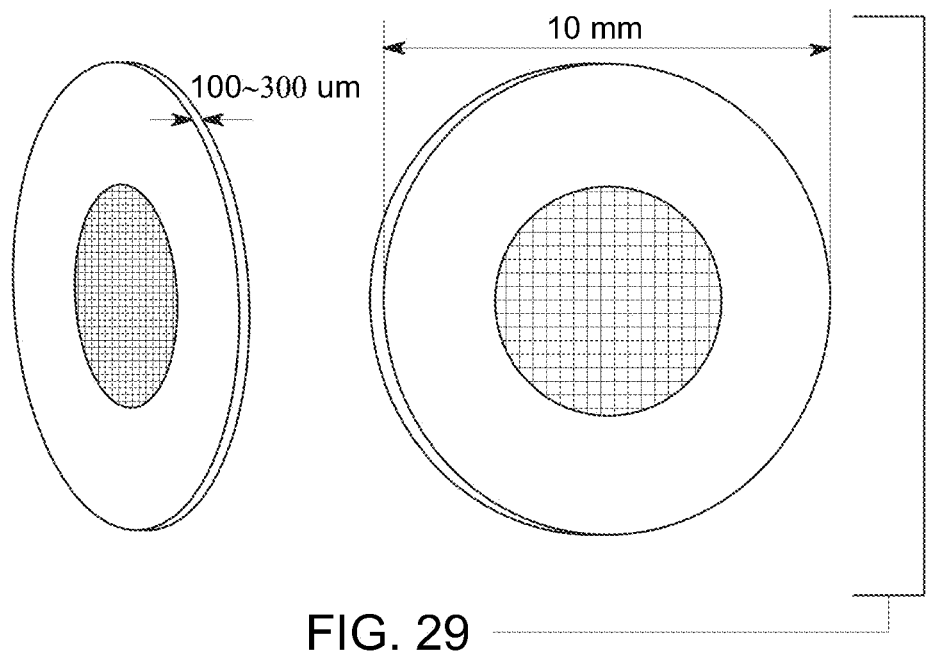

FIG. 29 shows a diagram of the 10 mm slicer grid structure with thickness of 100 um to 300 um.

Figure 30:
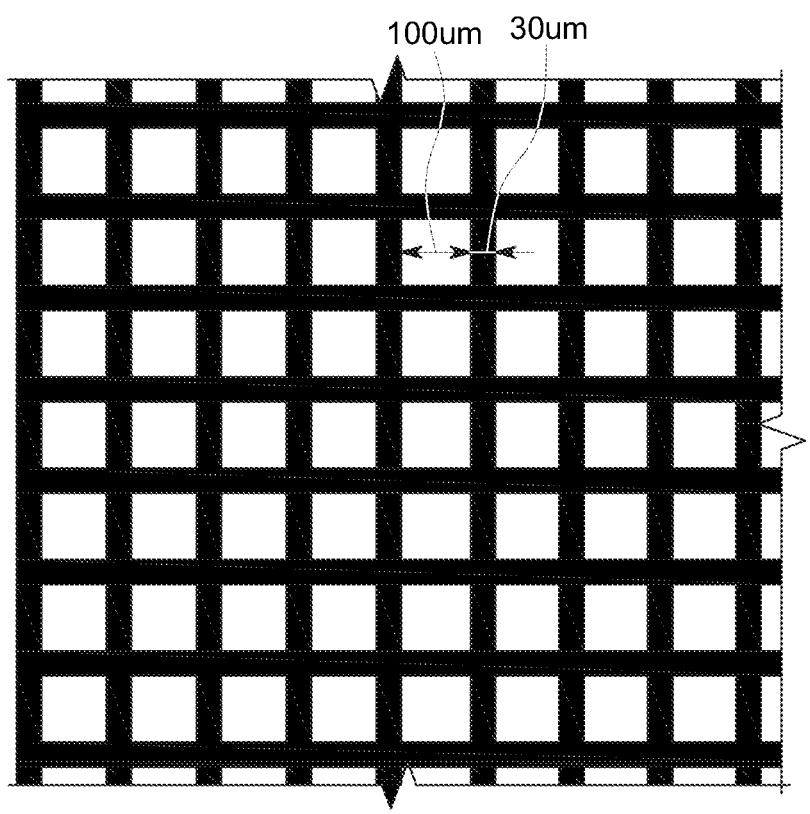

FIG. 30 shows a diagram of the square grid slicer with 100 um spacing between walls and 30 um wall thickness.

Figure 31:
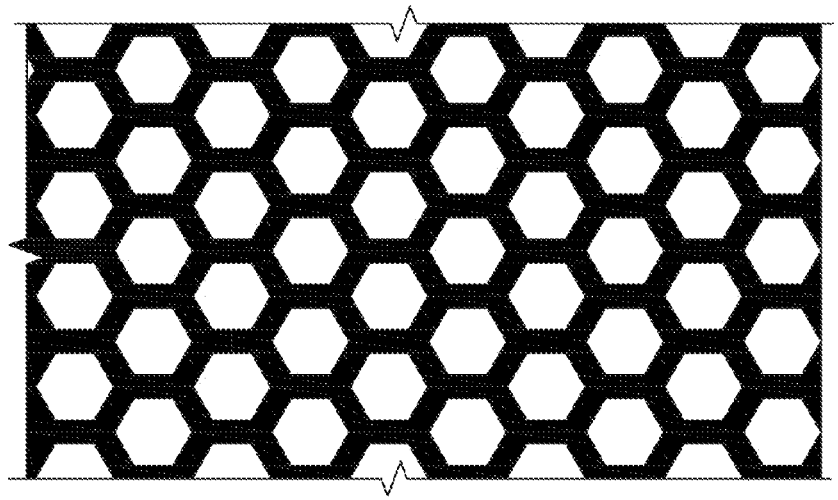

FIG. 31 shows a diagram of the hexagon grid slicer with 100 um spacing between walls and 30 um wall thickness.

Figure 32:
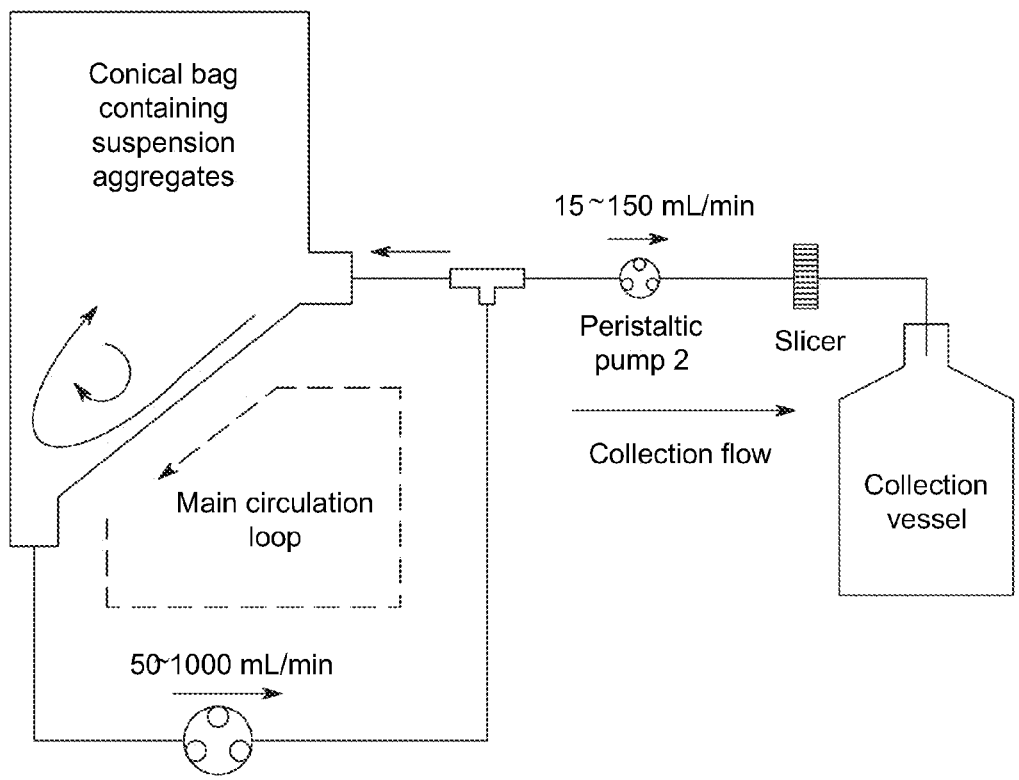

FIG. 32 shows a diagram of a method for closed system processing of aggregates through the slicer. A circulation loop driven by a pump and an in line conical bag suspends and distributes the aggregates. Tubing leading to the slicer is connected to the main circulation loop and a portion of the cell aggregates is delivered to the slicer through a second pump operating at a lower speed.

Figure 33:
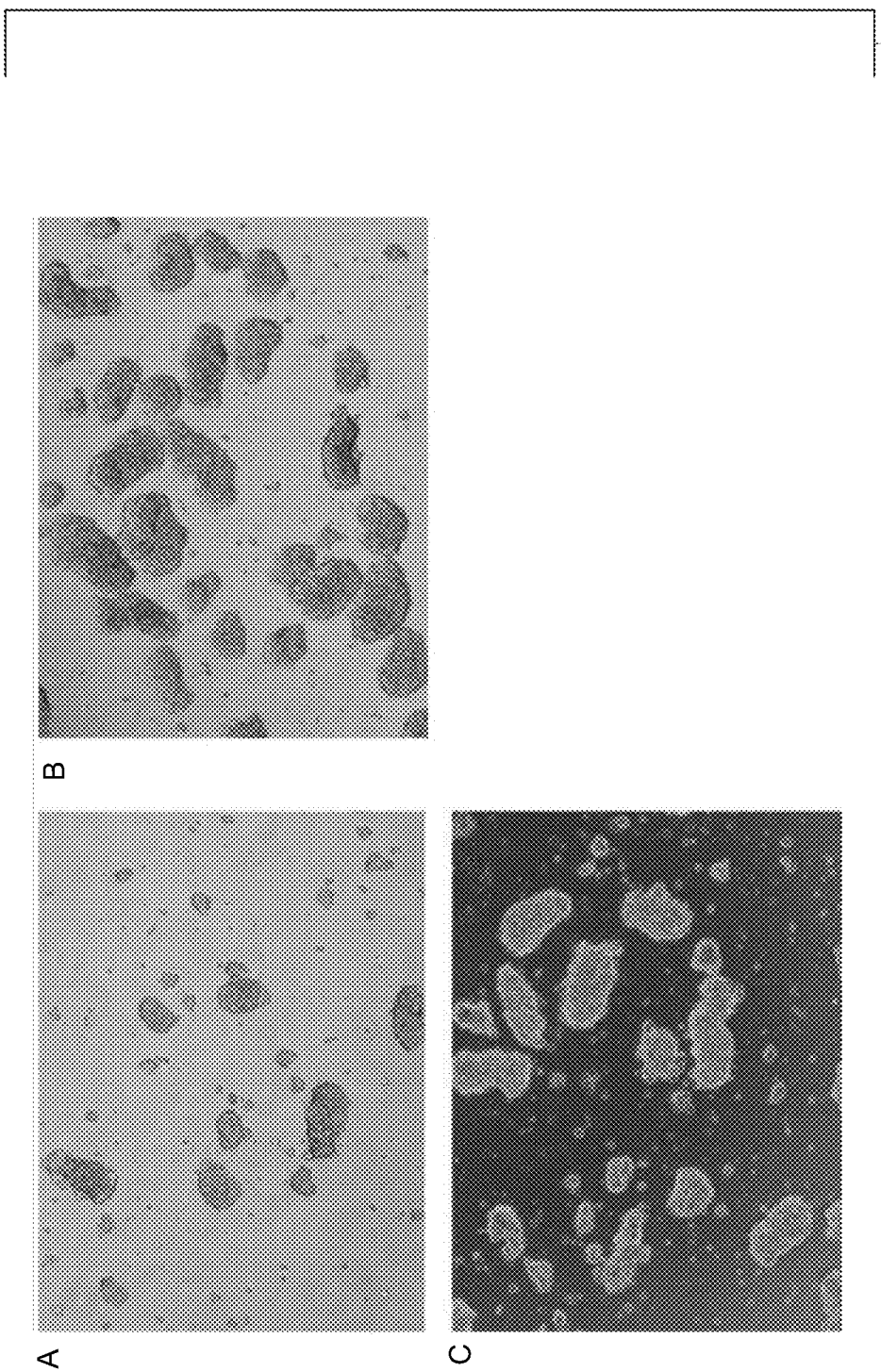

FIG. 33 shows images of the morphology of sliced aggregates of CT2 human embryonic stem cells.

Figure 34:
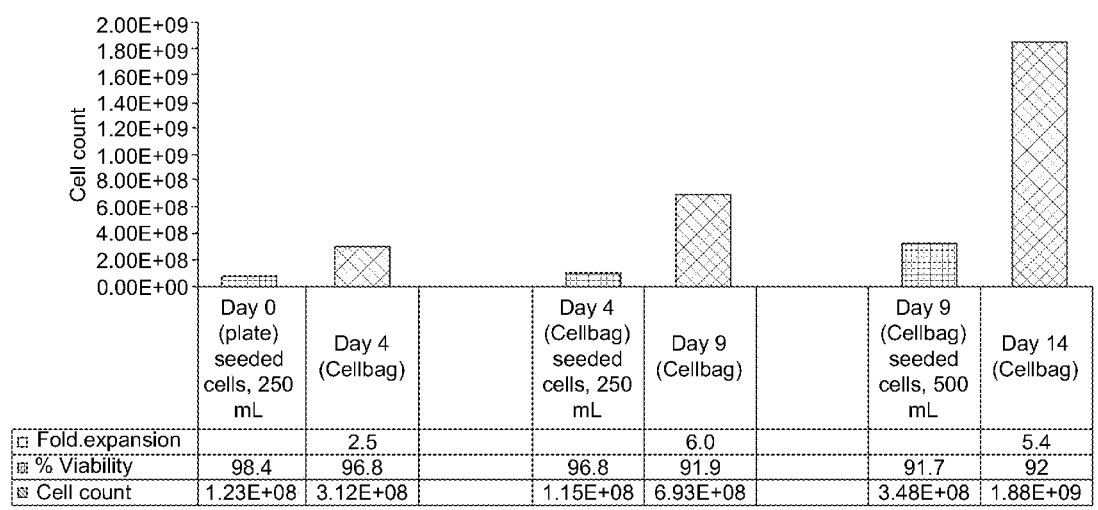
Figure 35:
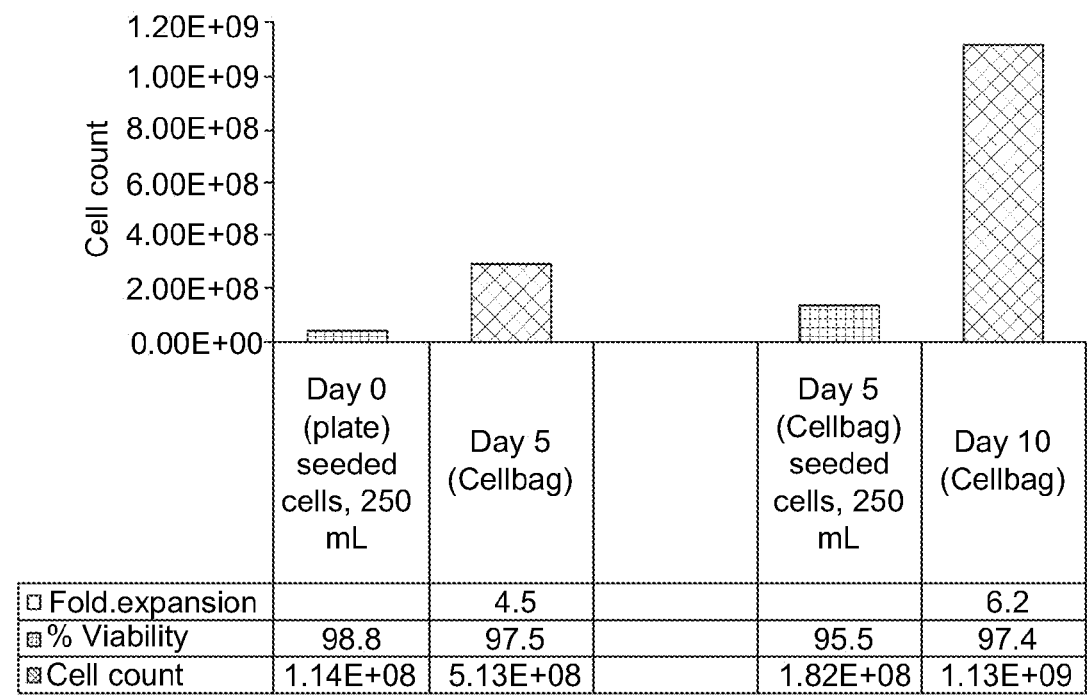
Figure 36:
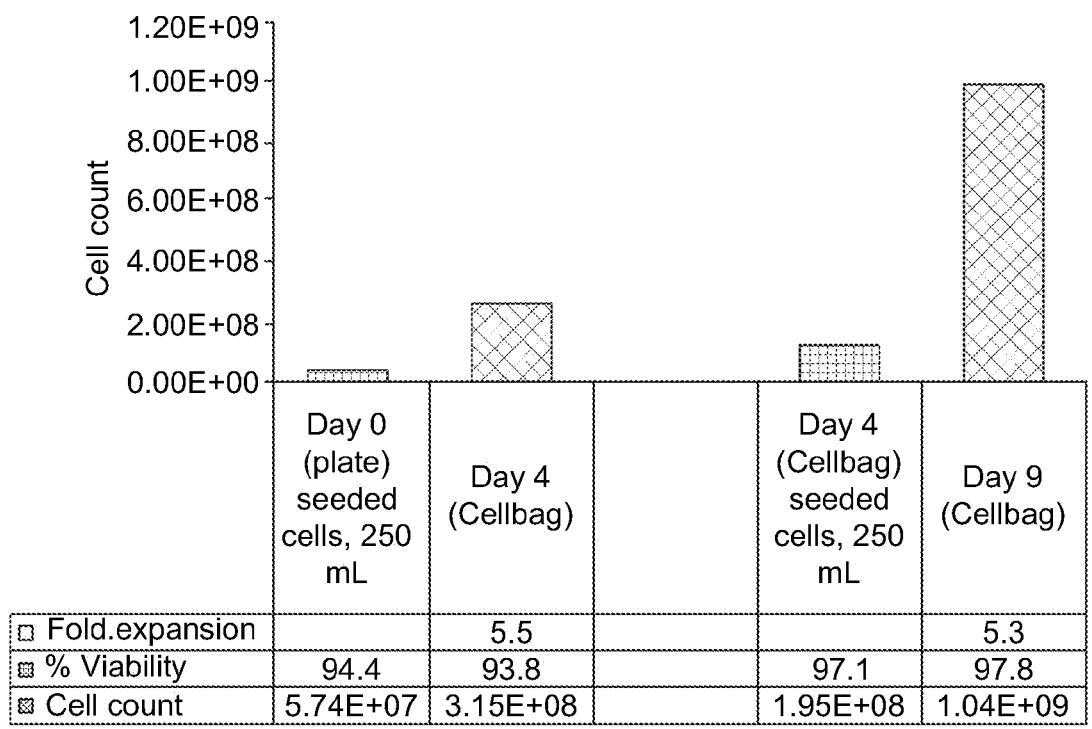
Figure 37:
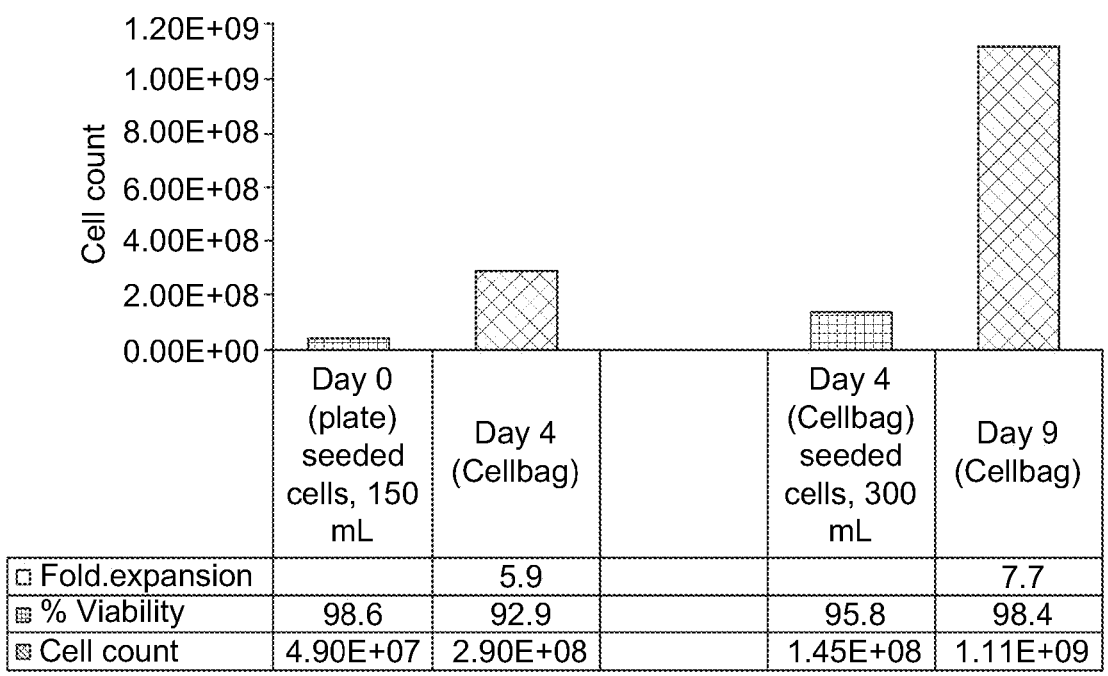
Figure 38:
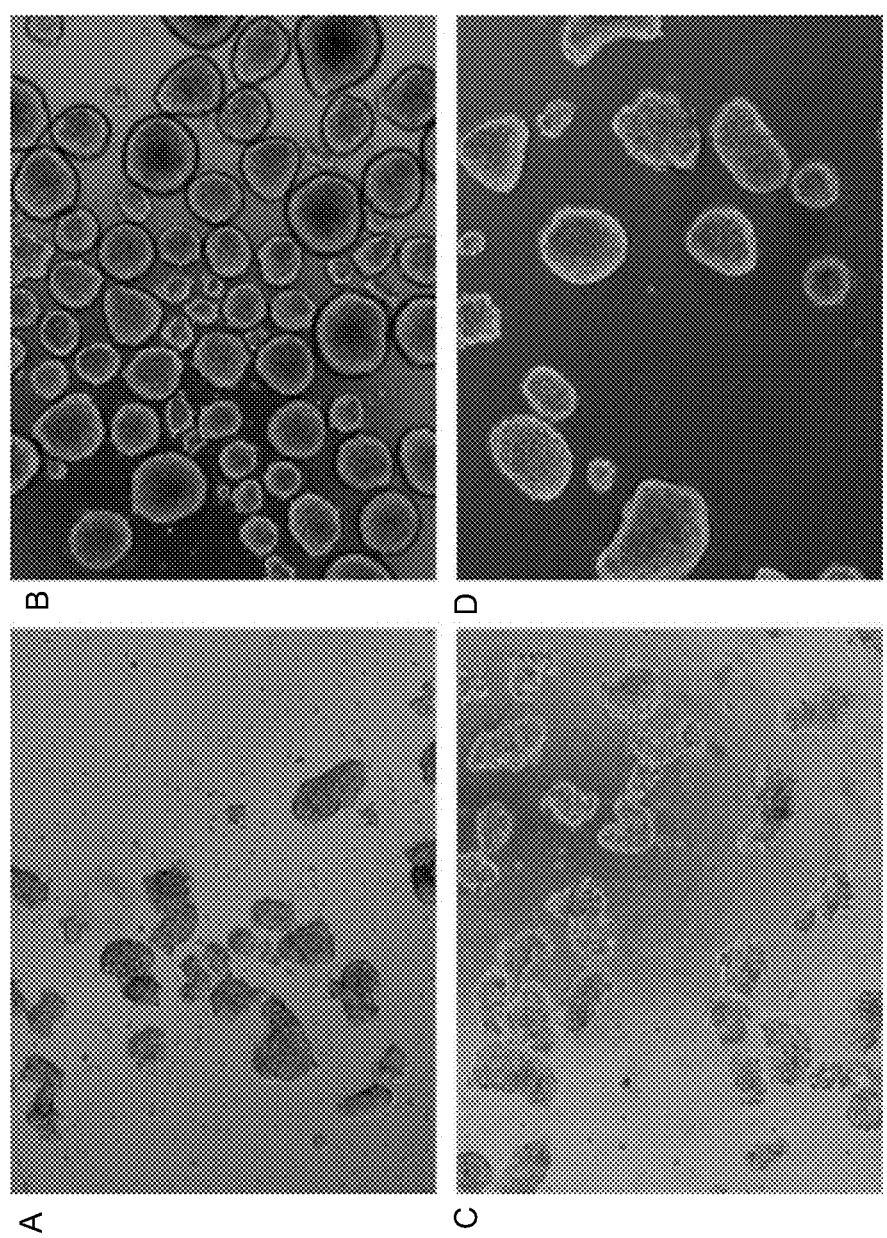

FIG. 34 shows the results of serial passaging of CT2 human embryonic stem cells using a nickel alloy hexagonal slicer grid. Serial passaging of CT-2 aggregates was carried out using nickel alloy hexagon slicer in 1 L Cellbag at 250 to 500 mL volume seeded with 2-5 uM ROCK inhibitor FIG. 35 shows the results of serial passaging of CT2 human embryonic stem cells using a nickel alloy square slicer grid. Serial passaging of CT-2 aggregates was carried out using nickel alloy square grid slicer in 1 L Cellbag at 250 mL volume seeded with 2-5 uM ROCK inhibitor FIG. 36 shows the results of serial passaging of CT2 human embryonic stem cells using a silicon hexagonal slicer grid. Serial passaging of CT-2 aggregates was carried out using silicon hexagon slicer in 1 L Cellbag at 250 mL volume seeded with 2-5 uM ROCK inhibitor FIG. 37 shows the results of closed system serial passaging of CT2 human embryonic stem cells using a silicon hexagonal slicer grid and circulation bag maintained in medium lacking Y27632 ROCK inhibitor. Serial passaging of CT-2 aggregates was carried out using silicon hexagon slicer in Cellbag at 250 mL to 300 mL volume without ROCK inhibitor FIG. 38 shows images of CT2 human embryonic stem cell aggregate morphology during closed system serial passaging in a Cellbag using a silicon hexagonal slicer and circulation bag. A) day 1, serial passage 1, B) day 4, serial passage 1, C) day 1 serial passage 2, D) day 5 serial passage 2.

DETAILED DESCRIPTION

"A" or "an" means herein one or more than one; at least one. Where the plural form is used herein, it generally includes the singular.

As used herein "perfusion" refers to the process of keeping culture cells alive by continuously feeding the cells with fresh media and removing spent media while keeping cells in culture.

"Aggregate" refers to an association of cells in which the association is caused by cell-cell interaction rather than adherence to a substrate. In an aggregate, two or more cells associate with each other by biologic attachments to one another. This can be through surface proteins, such as extracellular matrix proteins. In one embodiment, cells can be initially grown on a substrate where some cells associate with (adhere to) the substrate but further growth forms cell-cell associations (aggregation) that do not depend on association (adherence) of the further-grown cells with the substrate. In another embodiment, cells spontaneously associate in suspension to form cell-cell attachments independent of any adherence to a surface. A cellular feeder layer is also considered a substrate. So attachment of cells to a feeder layer is also a form of adherent culture (not an aggregate) since attachment of the cells is not to each other but to the cells in the feeder layer.

"Expansion" refers to the proliferation of a cell with or without differentiation and may include no passaging, one passage or more than one passage and/or serial passages.

"Stem cell" means a cell that can undergo self-renewal (i.e., progeny with the same differentiation potential) and also produce progeny cells that are more restricted in differentiation potential. Within the context of the disclosure, a stem cell would also encompass a more differentiated cell that has de-differentiated, for example, by nuclear transfer, by fusion with a more primitive stem cell, by introduction of specific transcription factors, or by culture under specific conditions. A "pluripotent stem cell" can potentially produce any cell or tissue the body needs to repair itself. Pluripotent stem cells are also able to self-renew, and can perpetually create more copies of themselves. Pluripotent stem cells include induced pluripotent stem cells (iPSCs) and embryonic stem cells (ESCs).

"Culture vessel" includes disposable and non-disposable plasticware, bags and/or containers and/or bioreactors. The term includes single-use plasticware, bags and/or containers and/or bioreactors and multiple-use plasticware, bags and/or containers and/or bioreactors.

"Closed system" refers to a culture vessel and accessory components that have been pre-sterilized while closed and/or sealed and retains integrity and/or sterility. The vessels and components are utilized without breach of the integrity of the system, permit fluid transfers in and/or out while maintaining asepsis, and are connectable to other closed systems without loss of integrity. A closed system bioreactor and/or vessel refers to a system in which cells, cell culture medium, chemicals and reagents are aseptically added, removed and/or manipulated without breach of integrity of the system (e.g., by opening the cap of a tube or lifting the lid off a cell culture plate or dish). Single-use or multiple-use bags and/or containers and/or bioreactors in a closed system are added onto or into the closed system for example by sterile tube welding at the site of the vessel or bioreactor.

A "subject" is a vertebrate, preferably a mammal, more preferably a human. Mammals include, but are not limited to, humans, farm animals, sport animals, and pets. Subjects in need of treatment by methods of the present invention include those suffering from a loss of function as a result of physical or disease-related damage.

The term "therapeutically effective amount" refers to the amount determined to produce any therapeutic response in a mammal. For example, effective amounts of the therapeutic cells or cell-associated agents may prolong the survivability of the patients. Alternatively, said treatment may be prophylactic and prevent and/or inhibit overt clinical symptoms. Treatments that are therapeutically effective within the meaning of the term as used herein, include treatments that improve a subject's quality of life even if they do not improve the disease outcome per se. Such therapeutically effective amounts are ascertained by one of ordinary skill in the art through routine application to subject populations such as in clinical and pre-clinical trials. Thus, to "treat" means to deliver such an amount.

"Treat," "treating" or "treatment" are used broadly in relation to the invention and each such term encompasses, among others, ameliorating, inhibiting, or curing a deficiency, dysfunction, disease, or other deleterious process, including those that interfere with and/or result from a therapy.

Large scale pluripotent stem cell culture is needed for pluripotent stem cell banking (e.g., for induced pluripotent stem cells), commercial production of cells (e.g., GE's Cytiva™ cardiomyocytes), and/or cell expansion for clinical trials. Pluritpotent stem cells may be induced pluripotent cell (iPS cells), "true" embryonic stem cell (ES cells) derived from embryos, embryonic stem cells made by somatic cell nuclear transfer (ntES cells), or embryonic stem cells from unfertilized eggs (parthenogenesis embryonic stem cells, or pES cells). Large scale cell feeder-free embryonic stem cell expansion in flasks is labor intensive, space prohibitive and separated populations may exhibit phenotypic drift. Therefore, there have been attempts in the field for developing alternative approaches for large scale pluripotent stem cell culture; e.g., CellSTACK® (Corning), Cell Factory (Nunc®) and bioreactors (microcarriers or suspension culture).

Differentiation of embryoid bodies (EBs) in a rocking platform has been demonstrated. Correia et. al. *Stem Cell Rev and Rep* (2014) 10:786-801. However, the three-dimensional structure of EBs presents challenges to directed differentiation and/or expansion. For instance, typically the exterior of EBs comprises an exterior "shell" consisting of tightly connected epithelial-like cells, and a dense extracellular matrix. Such structural features, in combination with EB size, create gradients of morphogens, metabolites, and nutrients, thereby reducing the effectiveness of directed expansion of EBs and results in increased heterogeneity and decreased efficiency of differentiated cell populations. Expansion of multipotent adult progenitor cell aggregates (MAPCs) in spinner flasks has been demonstrated (Subramanian et al., U.S. Pat. No. 8,609,406). However, the methods described by Subramanian et al. include steps such as enzyme digestion and centrifugation. Recently, suspension aggregate culture of pluripotent stem cells in an impeller stirred tank bioreactor system has been demonstrated (Chen, V C et. al, *Stem Cell Res.* 2012 May; 8(3):388-402) which obviates the need for any substrate or carriers in the bioreactor culture. In the Chen method for passaging cells from suspension culture, aggregates were harvested by centrifugation. By contrast, the methods provided herein allow for closed system expansion (including seed, perfusion and harvest) of pluripotent stem cells and/or pluripotent stem cell aggregates in a closed system using a rocking platform, which has not been demonstrated prior to the present work. Further, the methods described herein also allow for suspension and/or non-adherent cultures of pluripotent stem cells in closed systems without the use of membrane filters and/or centrifugation and/or enzyme digestion, which allows for maintenance of sterility in closed systems, reduces costs (e.g., for setting up centrifuges) and also reduces human intervention which assists in reducing cross contamination. Also contemplated within the scope of embodiments presented herein is the use of the present methods in combination with additional passages of the cells or cell aggregates which may include the use of membrane filters and/or centrifugation and the like and may include the use of enzyme digestion for dissociation of aggregates in the additional passages of the cells or cell aggregates.

Accordingly, described herein are methods for cell aggregate expansion, including human pluripotent stem cell expansion, in, for example, a Xuri™ W25 Cell Expansion system (the next generation Wave™ bioreactor system released in 2013) and in, for example, the legacy Wave bioreactor 2/10 system. The rocking motion of the platform induces waves in the culture fluid providing continual mixing and aeration, resulting in a robust environment for cell growth. The method employs culture vessels (e.g. the single use disposable Cellbags require no cleaning or sterilization) of varying sizes, providing ease of operation and protection against cross-contamination. Cellbags are typically available at 1, 2, 10, 20 and 50 L sizes for scalable cell culture. Optionally other Cellbags and/or vessels of larger or smaller volume can be employed for the methods described herein. Optical sensors are available for continuous monitoring of dissolved oxygen and pH, with real time controls and data storage. The platform software provides the ability to perform continuous or discontinuous perfusion/medium exchange in a closed system.

Typically, during perfusion, there are different ways to keep the cells in culture while removing spent media. One way is to keep the cells in the bioreactor by using capillary fibers or membranes, which the cells bind to. Another method is to not bind or adhere the cells, but rather utilize a "lily pad" floating filter that keeps the cells in the bioreactor while allowing the media to be removed. Another method is the use of a centrifuge to separate cells and return them to the bioreactor. Yet another method uses a physical approach such as acoustics to trap cells in the cell culture vessel or associated tubing while spent medium is removed.

By contrast, the methods described herein rely on gravity settling of cell aggregates which allows for removal of spent media without the use of filtration systems which are typically used to keep the cells in the bioreactor while concomitantly allowing the media to be removed. An advantage to this method is the loss of single cells and maintenance of aggregates, thereby increasing the overall quality and viability of the culture.

By continuously removing spent media and replacing it with new media, nutrient levels are maintained for optimal growing conditions and cell waste product is removed to avoid toxicity. When perfusion is carried out in a closed system using the methods described herein, the possibility of contamination is reduced. Advantageously, the closed systems and cell culture methods described herein utilize gravity-settling of cell aggregates thereby allowing for membrane-less filtration in the Cellbags which allows for reduction in losses due to adhesion of cells to filtration membranes and/or damage to cells due to shear during the filtration process.

The methods described herein are preferably employed in closed systems to minimize risk of culture contamination and cell cross-contamination and allow for reaching high viabilities and high cell densities with confidence. The methods described herein are designed for ease-of-use and reliability.

In the present methods, culture medium and cells contact only a presterile, chamber that is positioned on a special rocking platform. The rocking motion of the platform induces waves in the culture fluid and thereby provides continual mixing and oxygen transfer, resulting in a robust environment for cell growth. The system requires no cleaning or sterilization, providing ease of operation and protection against cross-contamination.

Provided herein are novel protocols to adapt cells from feeder free conditions on Matrigel™ to a suspension aggregate using a rocking motion. Typically a stirred tank reactor or spinner flask has been used to accomplish the adaptation. The methods described herein allow for cells to be maintained only using a rocking motion (from 6 well plate, to flask, to VueLife bag, to Xuri Cellbag). Provided herein are methods which demonstrate pluripotent stem cell expansion as suspension aggregates in a rocking motion system, with serial passage and up to 279-fold expansion. The fold expansion described herein is equivalent or better in perfusion Cellbags compared to expansions that have been reported using spinner flasks or stirred tank reactors. Provided herein are examples showing that the use of a culture vessel on a rocking platform in combination with a slicer for passaging is advantageous for expansion and serial passage of pluripotent stem cells in a unified closed system, specifically in reductions of time, reagents and labor. The slicer assembly of the invention could provide similar advantages to other non-rocking based bioreactor systems.

Also provided herein is a specific assembly of tubing connected to culture vessel (e.g., a Xuri Cellbag) that interacts with computer controlled peristaltic pumps to drive automated medium exchange. In one embodiment, the tubing is shaped like a T, with a lower vertical piece of tubing, a branch point, and two additional lengths of tubing connected at the branch point. The additional tubing is placed onto peristaltic pumps that are controlled by software. A slow harvest rate is used to draw off medium. The vertical nature of the tubing allows aggregates to gravity settle at rates that exceed the flow rate of the removed medium. The net effect is that aggregates remain in the optimal cell culture conditions in the vessel (e.g., a Xuri Cellbag) during the medium removal step. Medium removal can be continuous e.g., for up to 8 hours, up to 4 hours, and the like, but medium removal can be performed for much shorter or longer lengths of time. Following the medium removal step, fresh medium is rapidly added to the vessel (e.g., the Cellbag) over seconds to a few minutes or over any suitable length of time. The cycle of medium removal/rapid medium addition is repeated for the desired length of cell culture. In alternate instances, perfusion may be discontinuous and such embodiments are also contemplated within the scope of embodiments presented herein.

The automated perfusion design described herein is inherently low cost, is fully compatible with culture vessels, including the current Xuri system and Cellbags, can be adjusted to be fully compatible with any other culture vessel, and does not require any filters which would add cost and increase the risk for fouling and reduce performance. Further the automated perfusion described herein does not comprise moving parts or electronics which would increase complexity, cost, and risk for failure.

Provided herein are methods for expansion of cell aggregates in a closed system comprising
a cell culture vessel on a rocking platform bioreactor;
automated perfusion of cell aggregates in the vessel; and
membrane-free filtration of cell aggregates during the perfusion.

Also provided herein is a method for expansion of cell aggregates in a closed system comprising
a cell culture vessel on a rocking platform bioreactor;
aggregate formation in the vessel;
automated perfusion of cell aggregates in the vessel;
membrane-free filtration of cell aggregates during the perfusion; and
aggregate harvest and passaging in the closed system.

In some embodiments, the cell aggregates which are expanded are of plant, animal, insect or microbial origin. In some of such embodiments, the cell aggregates which are expanded comprise pluripotent stem cells or differentiated human cells.

In some instances, during the perfusion, the cell aggregates are retained in the bag in the absence of filtration membranes by gravity settling of cell aggregates.

Further, said automated perfusion is carried out in the closed system without human intervention, thereby reducing the possibility of contamination and allowing for maintenance of sterility during the expansion.

In some embodiments, the methods described above further comprise one or more additional expansions of the cell aggregates and/or progeny thereof by conducting serial passages. In some of such embodiments, the one or more of the additional expansions of the cell aggregates and/or progeny thereof, are carried out by passaging into a second vessel having a membrane filter.

In some embodiments, the methods described above comprise one or more additional expansions of the cell aggregates and/or progeny thereof where the one or more additional passages are conducted in the same vessel. In other embodiments, the methods described above comprise one or more additional expansions of the cell aggregates and/or progeny thereof where the one or more additional passages are conducted in a second vessel in the absence of a membrane filter in the culture vessel. In other instances, the methods described above comprise one or more additional expansions of the cell aggregates and/or progeny thereof where the one or more additional passages are conducted in a second vessel having a membrane filter (e.g., a floating membrane filter).

In such embodiments, the additional expansions and/or passages may be carried out in any order. By way of example, an initial passage may be carried out under membrane-free conditions in the culture vessel, followed by one or more additional expansions carried out in a culture vessel having a membrane filter. As an alternate example, one or more initial expansions and/or passages may be carried out in culture vessels which comprise membrane filters, followed by subsequent expansions and/or passages under membrane-free filtration conditions. Accordingly any sequence of expansions and/or passages comprising membrane-filtration or membrane-free filtration is contemplated within the scope of embodiments described herein where said sequence includes at least one expansion under the present membrane-free conditions.

In some embodiments, serial passaging of cell aggregates is enabled by enzyme-free passaging using slicer grids in the closed system. In some of such embodiments, the cell aggregates are dissociated with a slicer grid having blades separated by a distance of about 20 to about 500 microns. In some other embodiments, the cell aggregates are dissociated with a slicer grid having blades separated by a distance of about 100 microns. In some of such embodiments, the cell aggregates are dissociated with a slicer grid in line with tubing and a device for mixing of cell aggregates. In other words, in some embodiments, the cell aggregates are mixed in e.g., a conical bag, shown in FIG. 32, prior to dissociation with a slicer and the mixing bag is typically placed between the culture vessel and the slicer in the closed system.

The cell aggregate concentration used to pass through the slicer influences the recovery of sliced cell aggregates at high viability. Unexpectedly, it was found that slicing of cell aggregate concentrations below about $3 \times 10^6$ cells per mL produced higher viability samples with higher recovery than cell concentrations greater than about $3 \times 10^6$ cells per mL using a slicer geometry shown in FIGS. 29-31. Those skilled in the art will recognize that alternative slicer geometries will modify the threshold concentration that provides relatively higher viability and recovery. Fouling was minimized by maintaining a uniform suspension of aggregates in the flow stream, for example by using the mixing device shown in FIG. 32, resulting in higher cell viability and recovery. Advantageously, the use of a slicer obviates the need for the Y27632 ROCK inhibitor during expansion of sliced pluripotent stem cell aggregates, unlike enzymatically passaged pluripotent stem cell aggregates which generally requires agents such as the Y27632 ROCK inhibitor to maintain the viability of single pluripotent cells.

In one group of embodiments the slicer is coated with a hydrophobic material. In some embodiments, the slicer comprises a hydrophobic material.

In some other embodiments, serial passaging of the cell aggregates is enabled by disassociation of the cell aggregates in the closed system vessel in the presence of an enzyme In some embodiments of the methods described above, during the expansions and/or passages, the average diameter of each expanded cell aggregate is no more than about 800 micron in size. In some embodiments of the methods described above, during the expansions and/or passages, the average diameter of each expanded cell aggregate is no more than about 500 micron in size. In some embodiments of the methods described above, during the expansions and/or passages, the average diameter of each expanded cell aggregate is no more than about 400 micron in size. In some embodiments of the methods described above, during the expansions and/or passages, the average diameter of each expanded cell aggregate is no more than about 300 micron in size.

In some embodiments, the volume of the culture vessel is from about 50 mL to about 100 L. In some embodiments, the volume of the culture vessel is from about 50 mL to about 50 L. In some embodiments, the volume of the culture vessel is from about 100 mL to about 10 L. In some embodiments, the volume of the culture vessel is from about 100 mL to about 5 L. In some embodiments, the volume of the culture vessel is from about 150 mL to about 1 L. In some embodiments, the volume of the culture vessel is from about 50 mL to about 20 L. In some embodiments, the volume of the culture vessel is from about 200 mL to about 2 L.

Further provided herein is a method for passaging cell aggregates wherein cell aggregates are reduced in size by a slicer grid associated with a bioreactor in a closed system. In one group of embodiments for any method described herein, the cell aggregates are passaged in volumes exceeding 100 mL. In other words, passaging has generally been carried out in smaller volumes of culture medium and with lower cell counts. By contrast, the present methods allow for use of large volumes of culture medium in closed systems thereby allowing for passaging of cell aggregates in bioreactors and/or on industrial scale. The use of a slicer grid in combination with a bioreactor in a closed system for cell aggregate passaging in large volumes e.g., exceeding 100 mL has not been disclosed in the art prior to this disclosure. In another embodiment, the cell aggregates are passaged in volumes exceeding 250 mL, 500 mL, 1 L, 2 L or 5 L. In one embodiment, the slicer grid is a polygonal slicer grid. In one instance, said passaging of cell aggregates in volumes exceeding 100 mL is performed without the addition of a ROCK inhibitor (e.g., Y27632) to the medium.

In some embodiments of the method for passaging cells described above, the cell aggregates are dissociated with a slicer grid having blades separated by a distance of about 20 to about 500 microns. In some embodiments of the method for passaging cells described above, the cell aggregates are dissociated with a slicer grid having blades separated by a distance of about 100 microns. In some of such embodiments, the cell aggregates are dissociated with a slicer grid in line with tubing and a device for mixing of cell aggregates. In certain instances, the slicer is coated with a hydrophobic material. In other instances, the slicer comprises a hydrophobic material.

In some embodiments of the method for passaging cells described above, the average diameter of each cell aggregate prior to passaging is no more than about 800 micron in size. In some embodiments of the method for passaging cells described above, the average diameter of each cell aggregate prior to passaging is no more than about 500 micron in size. In some embodiments of the method for passaging cells described above, the average diameter of each cell aggregate prior to passaging is no more than about 400 micron in size. In some embodiments of the method for passaging cells described above, the average diameter of each cell aggregate prior to passaging is no more than about 300 micron in size.

Accordingly, the methods provided herein enable several workflows including and not limited to (1) Aggregate formation in bioreactors including e.g., Xuri Cellbag from these sources: enzymatically dissociated aggregates (e.g., Accutase™), cryopreserved stocks, and/or mechanically sliced aggregates (e.g., polygonal slicer grid); (2) Expansion method on rocking platforms: using well plates, T flasks and VueLife bags, non-perfusion bioreactor with tubing assembly for gravity settling (e.g., non-perfusion Cellbag), and/or perfusion bioreactor (e.g., floating membrane Cellbag); and (3) Serial Passaging: enzyme added to aggregates in cell culture vessel (e.g., Accutase™ in Cellbag), enzyme added to aggregates outside of cell culture vessel and/or mechanical passage using polygonal slicer grid.

Contemplated within the scope of embodiments provided herein is the use of the methods described herein for generating banks of cells, for generating expanded cell aggregates for research applications, for therapeutic and/or diagnostic testing (e.g., drug testing, toxicology or quality control assays in clinical trials), and/or for treatment of patients. Provided herein are methods comprising administering to subjects in need thereof a pharmaceutical composition comprising a pharmaceutically-acceptable carrier and at least one cell and/or cell aggregate obtained from the methods described herein.

Also provided herein is a method of treating a disorder in a subject in need of treatment by administering a therapeutically effective amount of the cells and/or aggregates produced in the methods above to the subject in need thereof. The methods further include a method of treating a disorder in a subject in need of treatment by administering a therapeutically effective amount of a pharmaceutical composition comprising a pharmaceutically-acceptable carrier and the cells and/or aggregates produced in the methods above. It will be understood that the methods described herein are applicable to pluripotent stem cells and also differentiated cells.

In some embodiments the purity and/or homogeneity of the expanded cells obtained from the methods described herein and/or for administration to a subject is about 100% (substantially homogeneous). In other embodiments the purity and/or homogeneity of the expanded cells obtained from the methods described herein and/or for administration to a subject is 95% to 100%. In some embodiments the purity and/or homogeneity of the expanded cells obtained from the methods described herein and/or for administration to a subject is 85% to 95%. In the case of admixtures with other cells, the percentage can be about 10%-15%, 15%-20%, 20%-25%, 25%-30%, 30%-35%, 35%-40%, 40%-45%, 45%-50%, 60%-70%, 70%-80%, 80%-90%, or 90%-95%.

The choice of formulation for administering the cells for a given application will depend on a variety of factors. Prominent among these will be the species of subject, the nature of the condition being treated, its state and distribution in the subject, the nature of other therapies and agents that are being administered, the optimum route for administration, survivability via the route, the dosing regimen, and other factors that will be apparent to those skilled in the art. For instance, the choice of suitable carriers and other additives will depend on the exact route of administration and the nature of the particular dosage form Final formulations of the aqueous suspension of cells/medium will typically involve adjusting the ionic strength of the suspension to isotonicity (i.e., about 0.1 to 0.2) and to physiological pH (i.e., about pH 6.8 to 7.5). The final formulation will also typically contain a fluid lubricant.

In some embodiments, cells are formulated in a unit dosage injectable form, such as a solution, suspension, or emulsion. Pharmaceutical formulations suitable for injection of cells typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof. The skilled artisan can readily determine the amount of cells and optional additives, vehicles, and/or carrier in compositions to be administered in methods of the invention.

Compositions can be administered in dosages and by techniques well known to those skilled in the medical and veterinary arts taking into consideration such factors as the age, sex, weight, and condition of the particular patient, and the formulation that will be administered (e.g., solid vs. liquid).

It is to be appreciated that a single dose may be delivered all at once, fractionally, or continuously over a period of time. The entire dose also may be delivered to a single location or spread fractionally over several locations.

In various embodiments, cells may be administered in an initial dose, and thereafter maintained by further administration. Cells may be administered by one method initially, and thereafter administered by the same method or one or more different methods. The levels can be maintained by the ongoing administration of the cells. Various embodiments administer the cells either initially or to maintain their level in the subject or both by intravenous injection. In a variety of embodiments, other forms of administration are used, dependent upon the patient's condition and other factors, discussed elsewhere herein. Suitable regimens for initial administration and further doses or for sequential administrations may all be the same or may be variable. Appropriate regimens can be ascertained by the skilled artisan, from this disclosure, the documents cited herein, and the knowledge in the art. The dose, frequency, and duration of treatment will depend on many factors, including the nature of the disease, the subject, and other therapies that may be co-administered. In any of the embodiments described herein, the cells may be differentiated or non-differentiated. In any of the embodiments described herein, the cells may be dissociated or aggregates. In any of the embodiments described herein the cells and/or cell aggregates may comprise a combination of pluripotent stem cells and progeny thereof.

EXAMPLES

Material and Methods

Materials: Aggregates were cultured in Xuri Cellbags with perfusion (28-9376-52) and without perfusion (CB0001L10-01). Medium bag for feed was 5 L Hyclone Labtainer (SH30713.01). Waste bag was Mbag from GE Healthcare (MB0020L10-01). Matrigel™ was purchased from BD Biosciences. Accutase™ was purchased from MP Biomedical (CA, USA) and Invitrogen™ (NY, USA); mTeSR™1 medium was purchased from STEMCELL™ Technology Inc. (Vancouver, BC, Canada). Y-27632 (ROCK Inhibitor) was purchased from Sigma Aldrich (St. Louis, Mo.) and Millipore®. CT2 hESC were obtained from Ren-He Xu at the University of Connecticut Health Center. CHB10 were obtained from George Daley, Children's Hospital Boston. NL5 iPSC were obtained from Guokai Chen at the NIH.

Methods: Human embryonic stem cells were adapted from Matrigel™ to suspension aggregates for greater than 5 passages prior to Xuri™ W25 experiments. Cells were maintained in mTeSR™1 on ultra-low attachment 6 well plates (Corning) rocked using a ThermoFisher VariMix test tube rocker. Stock cells were confirmed to be karyotypically normal. Serial passaging was performed using Accutase™ to reduce aggregates to small clusters and single cells. Cell counts and viability were determined using a Nucleocounter® NC200™ (Chemometec, Denmark).

Example 1

The human embryonic stem cell line CT2 (from Ren-He Xu at University of Connecticut) and the human induced pluripotent stem cell line NCRMS (also known as NL 5, from Guokai Chen at the NIH were suspension adapted from feeder-free cell stocks and maintained for at least 5 passages at small scale prior to bioreactor culture. Cells from actively expanding small scale cultures and from frozen stocks were seeded into a modified Cellbag that holds 150 mL volume. The single cells and small (<5 cell) clusters rapidly formed aggregates of roughly 100 μm diameter in the Cellbag, which expanded to roughly 250 μm diameter over 4 days. Half to full medium exchanges were performed daily and cells were harvested after 4 days of culture. Up to 5.5-fold expansion was observed in the 150 mL cultures. The cells recovered from 150 mL scale were dissociated in Accutase™ and were reseeded into a 2 L perfusion bag at 1 L volume. The cells were expanded for 4 days under perfusion conditions, with aggregates expanding to 300 to 350 um in diameter. Up to 9-fold expansion, representing approximately 4 million cells per mL, was obtained after 4 days. Cells were characterized by flow cytometry for the pluripotency markers Oct4, Tra-1-60 and SSEA3, by karyotype, and for embryoid body formation. In conclusion, our results describe successful expansion of suspension aggregate adapted pluripotent stem cell lines in the Xuri™ Cell Expansion system W25.

hESC Suspension Culture (A)

Suspension aggregate cultures of H1 and CT2 cells were established and frozen stocks were generated for each. It was determined that cells expand and maintain pluripotency (based on Oct4, Tra-1-60 and SSEA3 expression) better when cultured on low attachment plates than on standard cell culture plates. Suspension aggregate cultures were found to grow continuously for 5 weeks. Successful aggregate formation and expansion in 6 well plates, T25 and T75 flasks was demonstrated.

A number of experiments were performed to characterize seeding, aggregate formation and expansion rates. At the standard seeding density (400K per mL medium), doubling times are roughly 4× over 3 days. When seeded at 100K per mL, expansion rates are higher (up to 10-fold over 3 days). Expansion rates are generally lower when cells are seeded at higher densities. Seeding efficiencies appear to be >90%. Aggregates are able to reattach onto MG coated surfaces and regain normal hESC morphology.

hESC Suspension Culture (B)

Pluripotency markers during serial passaging of CT2 aggregates were found to be retained.

hESC Suspension Culture (C)

Cryopreserved cell banks of CT2 and H1 suspension aggregates were expanded, and CHB10 cryopreserved cell banks were expanded. Flow cytometry on CT2 and CHB10 showed high pluripotency marker expression. Monitoring of expansion rates for the cell lines was continued and typically 3 to 4-fold expansion was observed over 3 days and 6 to 8-fold expansion over 4 days. This is a slower growth rate than typically observed on Matrigel™.

Evaluation of scaled up aggregate culture from 6 well plates (35 mm) to 100 mm plates, and in T25 and T75 flasks was continued. The results showed a progressive drop in expansion rates as the vessel sizes scale up, which can be mitigated using smaller rock angles. It is likely that smaller rock angles may be required as the end to end distance of the vessel increases in size.

hESC Suspension Culture (D)

Successful seeding and expansion in Vue Life 32c and Vue Life 72c bags was demonstrated. 7-fold expansion was observed in 4 days in a Vue Life bag. The ability to serially passage hESC aggregates from one Vue 1Life 72c bag to another Vue Life 72c bag was demonstrated.

hESC Suspension Culture (E)

5 serial passages were successfully performed in VueLife 72 bags, with typical four day expansions between 5 and 7-fold and viabilities >90%.

hESC Suspension Culture (F)

Flow cytometric analysis of aggregates passaged for 5 passages in VueLife bags show similar high levels of Oct4 and Tra-1-60 expression compared to aggregates maintained on 6 well plates. However, there was a general reduction in pluripotency marker expression magnitude in all aggregates compared to CT2 on Matrigel™ (levels seen in historic controls).

hESC Suspension Culture

Successful expansion of CT2 (up to 5.3-fold) was demonstrated in four experiments. Cells were expanded in modified Wavebags at 150 mL volume, and maintained on the 2/10 platform. Flow cytometric analysis of aggregates expanded in the Wavebag showed >95% expression of Oct4, Tra-1-60 and SSEA3, demonstrating a pluripotent phenotype. Demonstrated aggregate formation in the Wavebag in three experiments on established NL-5 iPSC suspension aggregates.

hESC Suspension Culture (G)

Serial transplantation of CT2 from a modified Wavebag to a 1 L perfusion bag on the Xuri W25 system was demonstrated in two experiments. Up to 9-fold expansion was observed with perfusion at 1 L scale, and cell densities of 3.8M per mL were achieved. Approximately 40-fold expansion was observed over 8 days.

hESC Suspension Culture (H)

Demonstrated successful serial transplantation of CT2 in four successive passages from a modified Wavebag to modified Wavebag to modified Wavebag to a 1 L bag on the Xuri W25 system. The 1 L bag was not perfused, rather batch half medium changes were performed. Approximately 256-fold expansion was observed over 16 days. With perfusion, it is expected that the expansion rate would be higher. Demonstration of seed, feed (perfusion) and harvest on a Xuri W25 perfusion Cellbag was performed in a closed system, sterile process. Flow cytometry results show maintenance of pluripotency at normal levels in Xuri W25 expanded cells during serial passage. Cells retained a normal karyotype after serial passage.

hESC Suspension Culture

EB results show that Xuri W25 expanded cells retain the ability to differentiate into all three germ layers. Cells retained a normal karyotype after serial passage. Additional expansions of the pluripotent stem cell line CT2 were successfully carried out in WAVE 2/10 and Xuri W25 systems.

Methods:

Aggregates were initially established in ultra low attachment 6 well plates and expanded for 3-5 days before aggregates were dissociated to single cells/small clusters and reseeded into new wells. Seeding densities ranged from 100K to 800K per mL. Rocking angles used ranged from 15-25 degrees, with rock speeds of 15 to 25 rocks per minute. Preferred rocking angles range from 15-20 degrees with rock speeds of 20 rpm.

Individual pluripotent stem cell lines tolerate rocking angles differently. The CT2 line tolerates higher rock angles than the NL5 line. NL5 cells prefer rocking angles from 5-15 degrees and rock speeds of 15 to 25 rocks per min in 6 well plates. Preferred angles for NL5 range from 7 to 15 degrees, with best results at 9 degrees.

T25, T75 flasks, VueLife bags and Xuri Cellbags require a reduction in rocking angles compared to the 6 well plates. Typically rocking angles for flasks, VueLife bags and 2 L Cellbags had to be reduced by 3 to 7 degrees compared to the angle used for 6 well plates to drive seeding and expansion. Problems with using rock angles outside the range include a reduction in initial seeding (poor aggregate formation) and/or clumping of aggregates. Clumping of aggregates also occurs in corners of flasks and bags, and therefore having a rounded corner rather than a straight edge is advantageous. It was observed that the use of a paperclip on the corners of the VueLife bags reduced clumping by eliminating the corner edge.

Modified Wave bags were prepared by slicing the seam between cell culture chambers in a Dual bag and adding film to either end to create a modified Wavebag (Cellbag) that allows for smaller volume (up to 500 mL) cell culture volumes. Given the cost of the medium, initially lower volumes (150 mL) were chosen for the first studies. It was noted that expansion at 150 mL volumes is often lower than expansion at larger volumes in the modified Cellbag, which is likely attributable to the shape of the Cellbag after inflation. An overinflated bag has a different curvature to the cell culture area that can result in cells desiccating at the edges of the bag, resulting in cell losses. In addition, the increased curvature results in more clumping of aggregates reducing cell expansion.

Therefore, it was recognized that volumes in Cellbags may influence cell expansion, and that volumes greater than 150 mL in a modified Wavebag are preferred. Similarly, volumes of greater than 400 mL in a 1 L Cellbag are preferred. Cells were seeded into Celbags either from stock cells grown in 6 well plates, flasks, VueLife bags, or a prior Xuri Cellbag, or from cryopreserved stocks. In all cases, aggregates formed in the Cellbag and expansion was observed.

Closed system handling of cells was performed with some modifications to the commercial Cellbag. Specialized tubing sets (PVC and C-flex) were designed to the correct length and with the correct couplings to allow assembly of a medium bag, perfusion waste bag either in a sterile laminar flow cabinet or by sterile tube welding. The accutased single cells and small (<5 cell) clusters were seeded into the Cellbag inflated on the rocking platform. The bag holding the cells was sterile welded onto the tubing that connects to the Cellbag. The software controls operated perfusion (adding fresh medium and removing perfusion waste at 400 mL per day to 1 L per day). In non-perfusion bags, batch medium exchange was performed using gravity settling of cells and the Xuri system peristaltic pumps for removal of spent medium and addition of fresh medium. A description of the process is shown in the accompanying figures.

Accutase™ in the bag was performed by removing the majority of the growth medium through gravity settling of aggregates or through the perfusion filter. A PBS bag was sterile welded onto the Wave feed tubing line and the remaining volume in the Cellbag was washed with around 200 mL of PBS. The PBS was then removed either through gravity settling or perfusion filter and a bag with Accutase™ was added by sterile welding and cells were exposed to Accutase™ for 3 to 10 minutes in the Cellbag. A syringe was placed on a port that contained a dip tube and after the Accutase™ incubation the cells were pulled through the dip tube into the syringe to break the aggregates apart. While a syringe is not a closed system, various designs can be substituted including a sterile filter associated with the syringe to filter the air similar in design to the air filter already on the Cellbag.

Accordingly, one method for closed system medium exchange for suspension aggregates on Xuri W25 without perfusion filter would be as follows.

Pre warm medium in feed bag

Once pre-warmed, ensure that feed and harvest bags are tube fused.

Pause reactor, wait until it comes to a stop at a 12 degree angle

Lift tray to bring to 60 degree angle

Turn off gas flow then deflate bag by pushing on it
Let aggregates settle for 2 minutes
Harvest:
From top menu bar, select Manual→Execute manual instructions
Select Media control→Harvest→Tube inner diameter=3.2 mm→Insert
Select Pump Control→Start Harvest Pump→Limited→60 sec duration, 200 rpm→Insert
Execute.
Pump will pull off ~75 mL. Using 200 rpm, roughly 75 mL will be removed every 60 seconds. The calibration of the pumps can change and it's recommended to calibrate every 4 days.
Click on Close.
Feed:
From top menu bar, select Manual→Execute manual instructions
Select Media control→Feed→Tube inner diameter=3.2 mm→Insert
Select Pump Control→Start Feed Pump→Limited→65 sec duration, 200 rpm→Insert
Execute.
Pump will add ~75 mL. Using 200 rpm, roughly 75 mL will be added every 60 seconds. To ensure that all of the fresh medium is transferred to the bag and the tubing is empty, run 5 seconds longer than needed. The calibration of the pumps can change and it's recommended to calibrate every 4 days.
Click on close.

The protocol described above requires manual instructions to gravity settle cells. Alternatively, perfusion controls can be set using the Xuri control software, either using a continuous perfusion (~0.3 mL/min feed and removal for 500 mL/day) or discontinuous (with batch removals of 50-500 mL at a time and replacement of fresh medium) set to occur at least once a day. In some instances, discontinuous perfusion may be preferred if cell expansion is improved. FIG. 10 details the amount of fresh vs spent medium over time in various continuous and discontinuous perfusion scenarios. In all cases, medium exchange is fully automated requiring no user intervention.

The exemplary Xuri Cell Expansion Systems W5 and/or W25 described herein is designed for quick set-up and can be used with working culture volumes from about 150 ml to about 5 L or larger or smaller volumes as described herein. This compact unit is fitted with integral features such as aeration, heating, and temperature control. Other options include weight controllers for perfusion culture, dissolved oxygen amplifiers, and pH controllers.

Example 2

The expansion rates described here are examples and not intended to define performance or any inherent limitations of the invention, system or approach. Those skilled in the art will recognize that expansion rates are influenced by the cell lines used, formulation of medium used, medium volumes, medium exchange and perfusion schedules, initial seeding density and the culture conditions used. The examples that follow describe maximal cell concentrations of approximately 6 million cells per mL, however it is conceivable that higher cell concentrations may be achievable when using the methods described in these examples in combination with the variables mentioned in the preceding sentence. The examples utilize a Xuri Cellbag Wave motion bioreactor system, but those skilled in the art will recognize that other rocking platforms could also achieve similar performance Materials: The materials used for the subsequent examples include centrifuge tubes, Xuri Cellbag bioreactors (e.g., product 29108442 and CB0001L10-01) from GE Healthcare® (MA, USA). The rocking platforms associated with the Cellbags are the Xuri Cell Expansion System W25 and the Xuri Cell Expansion System W5 (formerly known as Wave 2/10). Accutase™ was purchased from MP Biomedical (CA, USA) and Invitrogen™ (NY, USA); mTeSR™-1 medium was purchased from STEMCELL™ Technology Inc. (Vancouver, BC, Canada). Y-27632 (Y27632 ROCK inhibitor) was purchased from Sigma Aldrich (St. Louis, Mo.) and Millipore®. The polygonal grid slicers and the tubing assembly for gravity settling used for passaging were manufactured specifically for this application and were not purchased through a commercial vendor.

Cells:

CT-2 cell line (human embryonic stem cells) was obtained from University of Connecticut, USA; CHB-10 cell line was obtained from George Daley, Children's Hospital Boston, USA; NL5 (also known as NCRM-5) cell line (human induced pluripotent stem cells) were obtained from Guokai Chen at the National Heart, Lung, and Blood Institute iPSC and Genome Engineering Core Facility.

Adaptation of Pluripotent Stem Cells from Adherent Culture to Suspension Aggregate Culture:

Three pluripotent stem cell lines (two embryonic stem cell lines CT2, CHB10 and one induced pluripotent stem cell line NL5) were adapted from adherent culture on Matrigel™ to suspension aggregates in a rocking culture system. To provide rocking at small scale, cells were maintained in 6 well plates or T flasks and rocked using a Thermo Varimax test tube rocker or Boekel Scientific Rocker II 260350 rocking platform maintained in a standard humidified $CO_2$ incubator. The cell lines were maintained over a few passages to permit stable cell cultures prior to expansion on the Xuri W25 system. For each cell line, conditions were systematically tested for preferred cell plating concentration, the rock angle, the rock speed, concentration of Y27632 ROCK inhibitor and the length of Accutase™ exposure during passaging. It was noted that all three cell lines preferred different culture conditions.

For the three different cell lines, cells dissociated with Accutase™ were seeded onto low attachment 6 well plates or T flasks at cell densities between 100K to 1.5M cells per mL in 1 to 10 uM Y27632 ROCK inhibitor to establish cultures with about 50 to about 200 um diameter aggregates that formed after overnight culture. Different seeding densities were tested when first establishing cultures to determine the preferred seeding density for each cell type. The preferred rock angle/rock speed for expansion of the different cell lines was systematically determined Across the three cell lines, the preferred culture conditions in 6 well plates and T flasks were approximately 10 to 25 rocks per minute (rpm), and a 12 to 20 degree rock angle.

Daily feeding of cells was used for optimal maintenance of pluripotency. A daily 50% to 100% medium exchange was used. To perform the medium exchange, aggregates were either centrifuged at 180×g for 1 minute or alternatively allowed to gravity settle for 2 to 5 minutes. Larger aggregates gravity settle faster than smaller aggregates. The supernatant was carefully removed and was replaced with fresh medium, and aggregates were suspended by gentle pipetting. The cell expansion rate was dependent on the seeded cell concentration, in which higher expansion rates were obtained with lower initial cell denisties.

Expansion and Passaging of Suspension Aggregate PSC in 6 Well Plates/T Flasks:

PSC suspension aggregates were passaged every 3 to 5 days, dependent upon the density of aggregates and the diameter. Aggregates were passaged when they were about 250 to 400 um diameter. As aggregates grow in diameter, the centers may become darker or may develop what appear to be holes or vacant areas in the aggregates. The cell count increased by about 4-12 fold during a 3 to 5 day culture.

To passage, aggregates were washed once in PBS followed by Accutase™ for 5 to 7 minutes at 37 C. Dissociated cells were centrifuged for 5 minutes at 200×g, then supernatant was carefully removed and replaced with complete medium to the desired cell concentration in 1-10 uM Y27632 ROCK inhibitor. Alternatively, aggregates were passaged using a slicer composed of a nickel alloy or silicon consisting of a square or hexagon grid pattern, with 100 um spacing between the walls.

In one example, aggregate formation and cell expansion was measured after passage with Accutase™ or with the square grid or hexagon grid slicer. After passaging, CT2 human embryonic stem cells were seeded in 6 well plates in 2 ml mTeSR1 at either 4×10^5 cells per mL or 1.5×10^6 cells per mL, with or without 10 uM Y27632 ROCK inhibitor. The plates were maintained on a Boekel Scientific Rocker II 260350 rocker platform in a standard cell culture incubator at 37 degrees C., 5% $CO_2$, with culture conditions of 20 rocks per minute at a 15 degree rock angle. Aggregates formed from the accutased cells after overnight culture. Each day, the spent mTeSR1 was completely removed and replaced with fresh mTeSR1 without Y27632 ROCK inhibitor. On day 4, the aggregates were recovered, dissociated with Accutase™ and enumerated using a Nucleocounter NC200. Roughly 8-fold expansion was observed for the cells plated at 4×10^5 per mL for aggregates passaged by Accutase™ (FIG. 16). A similar roughly 8-fold expansion was observed for aggregates after passage with the square or hexagon slicer (FIG. 16). Roughly 4-fold expansion was observed for the cells plated at 1.5×10^6 per mL for both cells passaged by Accutase™ (FIG. 17). A similar roughly 4-fold expansion was observed for aggregates after passage with the square or hexagon slicer (FIG. 17). At both initial cell densities, the expansion rates of slicer passaged aggregates cultured with or without Y27632 ROCK inhibitor were similar. The morphology of the aggregates over a four day culture period are depicted in FIGS. 18-22.

VueLife Bag Expansion Data:

In one example, CT2 human embryonic stem cell aggregates were dissociated using Accutase™. Day 1 CT2 aggregates were seeded into a VueLife 72 C gas permeable bag at 250,000 cells per mL in 72 mL of mTeSR1 plus 10 uM Y27632 ROCK inhibitor. The VueLife bag was placed in a standard incubator and was rocked using a Thermo Varimax test tube rocking platform. The culture conditions consisted of 20 rocks per minute, 9 degree rock angle, 37 degrees C., 5% CO2. A complete medium exchange was performed each day with fresh mTeSR1 without Y27632 ROCK inhibitor. On day 4, the aggregates were recovered from the Cellbag, and dissociated with Accutase™ to single cells/small clumps. The dissociated cells were enumerated using a Nucleocounter NC200. A total of 8.67×10^7 viable cells were recovered with the overall culture at 96.3% viability, representing a 4.8-fold expansion.

Seeding in Cellbag from Accutase™ Dissociated Cells:

Pluripotent stem cell suspension aggregates were dissociated by Accutase™. The accutased cell product consisted of a majority of small clumps of 2-10 cells and single cells. Cells were added to a Xuri Cellbag in a total volume between 125 mL and 500 mL in a 1 L Xuri Cellbag or 350 mL to 1 L in a 2 L Xuri Cellbag in mTeSR1 plus 1 to 10 uM Y27632 ROCK inhibitor. The seeding cell concentration was between 100,000 and 2 million cells per mL. The medium optionally contained 0.2% Pluronic F68. Aggregates spontaneously established over a 2 to 18 hour period after initial seeding.

In one example, CT2 human embryonic stem cell aggregates were dissociated using Accutase™. The cells were seeded into a 1 L Xuri Cellbag at 400,000 cells per mL in 283 mL of mTeSR1 plus 10 uM Y27632 ROCK inhibitor. The culture conditions consisted of 20 rocks per minute, 5 degree rock angle, 37 degrees C., 5% CO2. Aggregates of roughly 100-150 um diameter formed by the next morning. Half of the spent medium was replaced daily with fresh medium without Y27632 ROCK inhibitor. On day 4, the aggregates were recovered from the Cellbag, and dissociated with Accutase™ to single cells/small clumps. The dissociated cells were enumerated using a Nucleocounter NC200. A total of 4.41×10^8 viable cells were recovered with the overall culture at 98.6% viability, representing a 3.9-fold expansion.

In another example, CT2 human embryonic stem cell aggregates were dissociated using Accutase™ then cryopreserved. The cryopreserved stocks were thawed, seeded into a 1 L Xuri Cellbag at 400,000 cells per mL in 150 mL of mTeSR1 plus 10 uM Y27632 ROCK inhibitor. The culture conditions consisted of 20 rocks per minute, 5 degree rock angle, 37 degrees C., 5% $CO_2$. Aggregates of roughly 100-150 um diameter formed by the next morning. Half of the spent medium was replaced daily with fresh medium without Y27632 ROCK inhibitor. On day 4, the aggregates were recovered from the Cellbag, and dissociated with Accutase™ to single cells/small clumps. The dissociated cells were enumerated using a Nucleocounter NC200. A total of 2.76×10^8 viable cells were recovered with the overall culture at 96.1% viability, representing a 4.6-fold expansion.

PSC Expansion in a Cellbag and Xuri W25 Bioreactor Settings:

Not all pluripotent cell lines prefer the same culture conditions. The following parameters were used for PSC expansion in the Xuri W25 system, and those skilled in the art will recognize that other conditions will also provide PSC expansion in other vessels: Temperature 37 degrees C., $CO_2$ level 5%, ambient O2 (~21%) or a reduced $O_2$ level. All experiments were performed using a rock angle between 2.5 to 6 degrees, and a rock speed of 12 to 20 rpm, and those skilled in the art will recognize that other conditions will also provide PSC expansion.

Aggregates formed 2-12 hours after addition of single cells/small clumps to the Xuri Cellbag. The cells formed aggregates between about 50 and 200 um diameter. It was normal to obtain a distribution of aggregate diameters 50 um above and below the mean aggregate diameter. The majority of aggregates fell within that size range, however there were on occasion some larger aggregates of roughly 200 to 400 um that formed. Conditions that favor smaller aggregates are preferred as nutrient availability can be limited in larger aggregates, and the smaller aggregates provide a greater relative expansion in the culture.

The preferred conditions provide spherical aggregates with minimal clumping. It is important to balance the level of agitation in the Cellbag, as too much agitation will lead to shearing including deformation of aggregates and producing excessive numbers of non-aggregated single cells. Too little agitation will lead to clumping of aggregates.

In one example, CT2 human embryonic stem cells were dissociated by Accutase™ to single cells or small clumps of 5 or fewer cells. The dissociated cells were seeded into a Xuri Cellbag at 400,000 cells per mL, 150 mL mTeSR1. The culture conditions consisted of 20 rocks per minute, 5 degree rock angle, 37 degrees C., 5% CO2. Aggregates of roughly 100-150 um diameter formed by the next morning. Half of the spent medium was replaced daily with fresh medium without Y27632 ROCK inhibitor. On day 4, the aggregates were recovered from the Cellbag, and dissociated with Accutase™ to single cells/small clumps. The dissociated cells were enumerated using a Nucleocounter NC200. A total of $2.2 \times 10^8$ viable cells were recovered with the overall culture at 99.1% viability, representing a 7.0-fold expansion.

In another example, CT2 human embryonic stem cells were dissociated by Accutase™ to single cells or small clumps of 5 or fewer cells. The dissociated cells were seeded into a 2 L Xuri perfusion Cellbag at 400,000 cells per mL, 1 L mTeSR plus 10 uM Y27632 ROCK inhibitor. The culture conditions consisted of 20 rocks per minute, 5 degree rock angle, 37 degrees C., 5% CO2. Aggregates of roughly 100-150 um diameter formed by the next morning. Half of the spent medium was replaced daily via continuous perfusion with fresh medium without Y27632 ROCK inhibitor. On day 4, the aggregates were recovered from the Cellbag, and dissociated with Accutase™ to single cells/small clumps. The dissociated cells were enumerated using a Nucleocounter NC200. A total of $2.23 \times 10^9$ viable cells were recovered with the overall culture at 93.5% viability, representing a 5.6-fold expansion.

In another example, NL5 human induced pluripotent stem cells were dissociated by Accutase™ to single cells or small clumps of 5 or fewer cells. The dissociated cells were seeded into a 1 L Xuri Cellbag at 400,000 cells per mL, 250 mL mTeSR1 plus 10 uM Y27632 ROCK inhibitor. The culture conditions consisted of 20 rocks per minute, 4 degree rock angle, 37 degrees C., 5% CO2. Aggregates of roughly 200-300 um diameter formed by the next morning. Half of the spent medium was replaced daily with fresh medium without Y27632 ROCK inhibitor. On day 4, the aggregates were recovered from the Cellbag, and dissociated with Accutase™ to single cells/small clumps. The dissociated cells were enumerated using a Nucleocounter NC200. A total of $3.7 \times 10^8$ viable cells were recovered with the overall culture at 92% viability, representing a 3.7-fold expansion.

Tubing Assembly for Gravity Settling and Medium Exchange in Non-Perfusion Bags:

The conceptual construct of the tubing assembly is shown in FIGS. 23 and 24, and an image of the assembly on a Xuri Cellbag is shown in FIG. 25. The assembly provides the following functions including but not limited to the following: (1) removal of cell/cell culture medium mixture, (2) cell aggregate separation from outgoing cell culture medium, (3) cell culture medium addition, and (4) cell culture medium removal.

Removal of cell aggregate/cell culture medium mixture is accomplished through the use of a dip tube which enters through one of the ports available on a non-perfusion bag. The dip tube should be of sufficient length/orientation such that cells/media can be removed from the non-perfusion bag while it is installed and in operation on the Xuri platform. Cell aggregate separation from outgoing media is achieved by the introduction of a gravity settling chamber with sufficient length (height) and diameter to ensure adequate gravity setting during media removal. The design of this chamber is not limited to a large diameter tube; a tortuous path may also be integrated if necessary for satisfactory cell aggregate separation. Tubing for fluid addition/removal needs to be of adequate length to ensure attainment of connections to media/waste containers. Fluid removal is achieved by pulling out the medium through the fluid removal path while keeping the fluid addition path closed. Fluid addition is achieved by instilling fresh medium through the fluid addition path while keeping the fluid removal path closed.

Medium Exchange in Non-Perfusion Cell Culture Vessels:

Pluripotent stem cell cultures require frequent medium exchange. Closed system medium exchange was performed without need for removing the Cellbag from the rocking platform using two methods: 1) A manual process or 2) an automated process.

The manual process for medium exchange is as follows: A spent medium collection bag was sterile tube welded onto the Cellbag. The rocking platform was tilted to an upright 60 degree angle. Aggregates were allowed to gravity settle for 1-5 minutes in the Xuri Cellbag. Aggregate settling time is faster for larger aggregates than for smaller aggregates. Using a pump, 50% or more of the spent medium was removed from the Cellbag drawing medium from a port above the settled aggregates. Single cells, which are typically non-viable, were frequently lost in the removed medium. Care was taken to not disrupt the settled aggregates while removing medium. Aggregates were gently resuspended then prewarmed fresh medium was added to the Cellbag from a cell culture medium bag sterile welded onto the Cellbag. After 3 to 5 days, the aggregates were passaged.

The process for automated medium exchange in a non-perfusion bag is applicable to non-perfusion Cellbags of all sizes. For example, a 1 L non-perfusion Cellbag was modified with the tubing assembly for gravity settling to enable removal of 10 to 100 mL of spent medium over a 15 minute to 6 hour period followed by addition of 10 to 100 mL of fresh medium to the Cellbag. Control software regulated the rate of spent medium removal and fresh medium addition through the tubing assembly for gravity settling. A fresh medium bag and waste bag were aseptically attached to the Cellbag. The fresh medium bag was optionally stored in a refrigerator during the duration of cell culture. After 3 to 5 days, the aggregates were passaged.

In one example, CT2 human embryonic stem cell aggregates were passaged using a nickel alloy square grid slicer with 100 um spacing between the walls. The cells were seeded into a 1 L Xuri Cellbag at 725,000 cells per mL, 250 mL mTeSR1. The culture conditions consisted of 20 rocks per minute, 4 degree rock angle, 37 degrees C., 5% $CO_2$. The perfusion conditions were designed to remove 15 mL of spent medium from the bioreactor over 50 minutes followed by addition of 15 mL in 1 minute such that 125 mL was replenished per day using the tubing assembly for gravity settling in non-perfusion bags. On day 4, aggregates were recovered from the Cellbag, and dissociated with Accutase™ to single cells/small clumps. The dissociated cells were enumerated using a Nucleocounter NC200. A total of $1.13 \times 10^9$ cells were recovered with the overall culture at 97.4% viability, representing a 6.2-fold expansion.

Medium Exchange in Perfusion Cellbags:

Automated PSC expansion was achieved using a perfusion Cellbag that contains a floating membrane within the Cellbag for removal of spent medium and retention of cells in the Cellbag. This protocol is applicable to all types of perfusion vessels, for example Cellbags with a floating membrane for perfusion. For example, 350 mL to 1 L volumes are typically cultured and perfused in a 2 L floating membrane perfusion Cellbag. Protocols for continuous and discontinuous perfusion are described below.

For continuous perfusion in a perfusion Cellbag, the weight based Xuri W25 Unicorn software control was used to maintain the volume in a Cellbag at a specific level, regulating continuous spent medium removal and fresh medium addition using the medium controls. In this method, the weight of the bag was continually monitored to regulate the rates of fresh medium addition and spent medium removal. In another method, pumps are programmed to add fresh medium and remove spent medium at a defined rate independent of a weight measurement. Preferably, the volume of spent medium removed is equal to the volume of fresh medium added in order to maintain a constant volume, however the two rates can be different.

For discontinuous perfusion, the software controls regulate the removal of a specific amount of spent medium and the addition of fresh medium. This approach is typically independent of the vessel weight. Preferably, a predefined volume of spent medium is removed followed by bolus addition of a volume of fresh medium, according to a pre-defined feeding schedule. For example, the feeding schedule could be set to remove 50 mL of spent medium every 2 hours, followed by an addition of 50 mL of fresh medium.

In one example, CT2 human embryonic stem cell aggregates were dissociated using Accutase™. The cells were seeded into a 2 L Xuri perfusion Cellbag with a floating membrane at 272,000 cells per mL in 1 L of mTeSR1 plus 10 uM Y27632 ROCK inhibitor. The culture conditions consisted of 20 rocks per minute, 5 degree rock angle, 37 degrees C., 5% $CO_2$. Aggregates of roughly 100-150 um diameter formed by the next morning. A continuous perfusion protocol was used to exchange 500 mL of mTeSR1 without Y27632 ROCK inhibitor per day using the Xuri W25 software controls. On day 4, the aggregates were recovered from the Cellbag, and dissociated with Accutase™ to single cells/small clumps. The dissociated cells were enumerated using a Nucleocounter NC200. A total of $2.59 \times 10^9$ viable cells were recovered with the overall culture at 95% viability, representing a 9.5-fold expansion.

Two methods for enzymatic aggregate passaging are: 1) closed system enzymatic treatment in the Cellbag, and 2) recovery of cells from the Cellbag followed by open enzymatic passaging external to the Cellbag. Both methods are described below. The open passaging method can be achieved in less time with fewer sterile bag welds needed. The closed system method allows maintenance of aggregates in a closed system throughout passaging.

Method for Accutase™ Dissociation of Aggregates in the Cellbag:

In this method, culture medium is removed, aggregates are washed in PBS, then treated with Accutase™ in the Cellbag. A method to break apart aggregates using shear is required.

A closed method for passaging suspension aggregates in a Xuri Cellbag is described. After lifting the Xuri platform tray to the 60 degree angle, aggregates were allowed to gravity settle for 1-5 minutes. Aggregate settling time is faster for larger aggregates than for smaller aggregates. A pump was used to remove the majority of medium from the Cellbag as possible without disrupting the settled aggregates. Preferably, the volume was reduced to 25 to 50 mL. A bag containing PBS prewarmed to 37° C. was sterile tube welded onto the Cellbag to wash cells. 250 mL to 500 mL of PBS was added to the Cellbag to wash cells. Aggregates were mixed in PBS then allowed to gravity settle for 1-5 minutes. A pump was used to remove as much PBS from the Cellbag without disrupting the settled aggregates. Preferably, the volume was reduced to 25 to 50 mL. An additional 250 mL to 500 mL of PBS was added to the Cellbag to wash cells a second time. Aggregates were mixed in PBS then allowed to gravity settle for 1-5 minutes. A pump was used to remove as much PBS from the Cellbag without disrupting the settled aggregates. Preferably, the volume was reduced to 25 to 50 mL.

A bag containing Accutase™ prewarmed to 37° C. was sterile tube welded onto the Cellbag. 50 mL of Accutase™ was added to the Cellbag and incubated while rocking at 37° C. A syringe attached to a 0.22 um filter tubing assembly on a Cellbag port was used to break apart the aggregates in Accutase™. 50 mL of complete medium was added and cells were collected for downstream applications.

In one example, CT2 human embryonic stem cells were dissociated by Accutase™ to single cells or small clumps of 5 or fewer cells. The dissociated cells were seeded into a Xuri Cellbag at 400,000 cells per mL, 150 mL mTeSR1 plus 10 uM Y27632 ROCK inhibitor. The culture conditions consisted of 20 rocks per minute, 5 degree rock angle, 37 degrees C., 5% $CO_2$. Aggregates of roughly 100-150 um diameter formed by the next morning. Half of the spent medium was replaced daily with fresh medium without Y27632 ROCK inhibitor. On day 4, the aggregates were dissociated with Accutase™ inside the Cellbag as described above. The dissociated cells were enumerated using a Nucleocounter NC200. A total of $4.2 \times 10^8$ viable cells were recovered with the overall culture at 97.8% viability, representing a 7.0-fold expansion.

Method for Accutase™ Dissociation of Aggregates Outside of the Cellbag:

Alternatively, aggregates were recovered from the vessel and passaged in an open system. This method was performed in two ways: 1) collection of the entire culture volume of cells from the vessel, or 2) removing the majority of the medium from the Xuri Cellbag after the aggregates gravity settled within the bag, then the aggregates were either washed in the bag with PBS or collected from the bag for washing/Accutase™ outside of the bag.

In one example, a method for open Accutase™ using a Xuri Cellbag is described. After lifting the Xuri platform tray to the 60 degree angle, aggregates were allowed to gravity settle for 1-5 minutes. Aggregate settling time is faster for larger aggregates than for smaller aggregates. A pump was used to remove the majority of medium from the Cellbag without disrupting the settled aggregates. Preferably, the volume was reduced to 25 to 50 mL. A collection bag was tube fused onto the system and a pump was used to transfer aggregates from the Cellbag into the collection bag. The collection bag was brought into a laminar flow cabinet and the aggregates were aseptically transferred to a conical tube. The conical tube was centrifuged at 180×g for 1 minute then supernatant was carefully removed. Aggregates were washed in PBS, centrifuged again at 180×g for 1 minute, then supernatant was removed. To dissociate the aggregates, Accutase™ was added for 5 to 7 minutes at 37° C.

Serial Passage: Filter-Less Bag to Floating Membrane Perfusion Bag Enzymatic Passage:

In one example, serial passaging of suspension aggregate pluripotent stem cells from a filterless bag to a floating membrane perfusion bag was performed. The first passage was expanded at 250 mL volume and the second passage was expanded in 1 L volume. CT2 human embryonic stem cell aggregates were dissociated using Accutase™. In each passage, cells were seeded into a 1 L non-perfusion or 2 L perfusion Xuri Cellbag at 400,000 cells per mL in mTeSR1 plus 10 uM Y27632 ROCK inhibitor. The culture conditions consisted of 20 rocks per minute, 5 degree rock angle, 37 degrees C., 5% $CO_2$. Aggregates of roughly 100-150 um diameter formed by the next morning. Half of the spent medium was replaced daily with fresh medium without Y27632 ROCK inhibitor in the filterless bag, and a continuous perfusion protocol was used to exchange 500 mL of medium per day using the Xuri W25 software controls in the floating membrane perfusion Cellbag. Aggregates were passaged on day 4 after seeding by dissociation with Accutase™ to single cells/small clumps. The dissociated cells were enumerated using a Nucleocounter NC200. In passage 1, a total of $6.96 \times 10^8$ viable cells were recovered with the overall culture at 99.4% viability, representing a 7-fold expansion (FIG. 26). In passage 2, a total of $2.23 \times 10^9$ viable cells were recovered with the overall culture at 93.5% viability, representing a 5.6-fold expansion. Over 8 days, there was an overall 39.2-fold expansion.

Serial Passage: Four Consecutive Enzymatic Serial Passages in Xuri Cellbags:

In one example, serial passaging of suspension aggregate pluripotent stem cells for four passages was performed in 1 L and 2 L Xuri Cellbags. Two passages were expanded at 150 mL volume, followed by one passage at 400 mL volume, and one passage in a 1 L volume. CT2 human embryonic stem cell aggregates were dissociated using Accutase™. In each passage, cells were seeded into a Xuri Cellbag at 400,000 cells per mL in mTeSR1 plus 10 uM Y27632 ROCK inhibitor. The culture conditions consisted of 20 rocks per minute, 5 degree rock angle, 37 degrees C., 5% $CO_2$. Aggregates of roughly 100-150 um diameter formed by the next morning. Half of the spent medium was replaced daily with fresh medium without Y27632 ROCK inhibitor. Aggregates were passaged on day 4 after seeding by dissociation with Accutase™ to single cells/small clumps. The dissociated cells were enumerated using a Nucleocounter NC200. In passage 1, a total of $2.19 \times 10^8$ viable cells were recovered with the overall culture at 99.1% viability, representing a 3.7-fold expansion (FIG. 27). In passage 2, a total of $4.17 \times 10^8$ viable cells were recovered with the overall culture at 97.8% viability, representing a 7-fold expansion. In passage 3, a total of $5.64 \times 10^8$ viable cells were recovered with the overall culture at 97.2% viability, representing a 3.5-fold expansion. In passage 4, a total of $1.25 \times 10^9$ viable cells were recovered with the overall culture at 94.4% viability, representing a 3.1-fold expansion. The overall expansion was 279-fold over 16 days. Aggregate morphology during the serial passage is shown in FIG. 28.

Slicer Design:

The slicer can be composed of a variety of biocompatible materials. The material must be amenable to sterilization, and have mechanical strength that allows it to withstand the stress experienced during flow of the cellular samples. The two materials tested for pluripotent stem cell aggregate passaging were nickel alloy and silicon. Those skilled in the art will recognize that other materials have properties that enable the desired slicer performance for aggregate passaging. The slicer is designed with a polygonal grid-like pattern, for example a square or hexagonal grid, with spacing between the walls of the grid between 50 microns and 400 microns (FIG. 29-31). In some experiments, the slicer was coated with a hydrophobic material to reduce shearing and fouling. For the pluripotent stem cell aggregate passaging experiments described below, square and hexagonal grids with 100 um spacing were used. The slicer was mounted in line with tubing that permitted the sterile flow of aggregates through the tubing and across the slicer in a closed system. The slicer may be integrated into the closed system by various fastening mechanisms including, but not limited to adhesive, molten polymer flow, or clamping. In a preferred method, aggregates are maintained in suspension via a circulation loop driven by a pump and an in line conical bag (FIG. 32). Tubing leading to the slicer is connected to the main circulation loop, and a fraction of the cell aggregates in the circulation loop is delivered to the slicer through a second pump operating at a lower speed than the pump controlling the circulation loop. The sliced aggregates can be collected in a separate vessel, or reintroduced into the same vessel.

Slicer Performance During Cellular Aggregate Passaging:

Aggregates were passed across the slicer in a flow stream consisting of 100 mL to 1 L volumes. A benefit of the slicer compared to enzymatic passaging is a reduction in time, labor and reagents. Successful slicing down to roughly 100 um dimension was achieved by one or more passes through the slicer in a unidirectional or bidirectional flow. The flow rate was controlled to minimize shear. Aggregate slicing performance for size reduction, maintenance of cell viability and subsequent expansion were demonstrated on pluripotent stem cell aggregates passed through the slicer at flow rates of 15 to 150 mL/min Those skilled in the art will recognize that good performance can also be achieved at other flow rates. The cell aggregate concentration used to pass through the slicer was determined to influence the recovery of sliced cell aggregates at high viability. Fouling of the slicer can result in reduced cell recovery and viability. It was determined that slicing of cell aggregate concentrations below about $3 \times 10^6$ cells per mL produced higher viability samples with higher recovery than cell concentrations greater than about $3 \times 10^6$ cells per mL. Fouling was minimized by maintaining a uniform suspension of aggregates in the flow stream, for example by using the mixing device shown in FIG. 32, resulting in higher cell viability and recovery. Sample images of sliced aggregates are shown in FIG. 33. The aggregate morphology after slicing includes irregular shapes, cuboidal shapes and spherical shapes. For 100 um slicers, at least one dimension of the aggregate is reduced to roughly 100 um diameter. Sliced aggregates were cultured in mTeSR1 and optionally 1 to 10 uM Y27632 ROCK inhibitor and allowed to expand. Y27632 ROCK inhibitor was not required for expansion of sliced pluripotent stem cell aggregates, unlike enzymatically passaged pluripotent stem cell aggregates which generally requires agents such as Y27632 ROCK inhibitor to maintain the viability of single pluripotent cells. The morphology of the sliced aggregates rapidly reformed a spherical shape under continued rocking culture conditions. The expansion rate of sliced aggregates was similar to the expansion rate of enzymatically passaged cells (FIGS. 16 and 17). Aggregates can be passaged by the slicer without PBS wash required for enzymatic passaging, therefore passaging by slicing takes less time and less overall effort than enzymatic passaging. Those skilled in the art will recognize that the slicer function and performance is not dependent upon the Xuri Cellbag bioreactor platform, and is compatible with other types of bioreactors including but not limited to other rocking motion platforms or stirred tank bioreactors.

Expansion of Aggregates after Slicer:

In one example, CT2 human embryonic stem cell aggregates were passaged using a nickel alloy hexagonal grid slicer with 100 um spacing between the walls. The cells were seeded into a Xuri Cellbag at 460,000 cells per mL in 250 mL mTeSR1 plus 3 uM Y27632 ROCK inhibitor. The culture conditions consisted of 20 rocks per minute, 4 degree rock angle, 37 degrees C., 5% $CO_2$. The perfusion conditions were designed to remove 15 mL of spent medium from the bioreactor over 50 minutes followed by addition of 15 mL fresh mTeSR1 without Y27632 ROCK inhibitor in 1 minute such that 125 mL was replenished per day using the tubing assembly for gravity settling in non-perfusion bags. On day 5, aggregates were recovered from the Cellbag, and dissociated with Accutase™ to single cells/small clumps. The dissociated cells were enumerated using a Nucleocounter NC200. A total of $6.9 \times 10^{\wedge}8$ viable cells were recovered with the overall culture at 91.9% viability, representing a 6.0-fold expansion.

In another example, CT2 human embryonic stem cell aggregates were passaged using a silicon hexagonal grid slicer with 100 um spacing between the walls. The cells were seeded into a Xuri Cellbag at 200,000 cells per mL in 250 mL mTeSR1 with no Y27632 ROCK inhibitor added. The culture conditions consisted of 20 rocks per minute, 4 degree rock angle, 37 degrees C., 5% $CO_2$. The perfusion conditions were designed to remove 30 mL of spent medium from the bioreactor over 110 minutes followed by addition of 30 mL fresh mTeSR1 without Y27632 ROCK inhibitor in 2 minutes such that 125 mL was replenished per day using the tubing assembly for gravity settling in non-perfusion bags. On day 4, aggregates were recovered from the Cellbag, and dissociated with Accutase™ to single cells/small clumps. The dissociated cells were enumerated using a Nucleocounter NC200. A total of $2.90 \times 10^{\wedge}8$ viable cells were recovered with the overall culture at 92.9% viability, representing a 5.8-fold expansion.

Serial Passage: Filter-Less Bag to Filter-Less Bag Passaging with Nickel Alloy Hexagonal Grid Slicer In one example, serial passaging of suspension aggregate pluripotent stem cells for three passages was performed in 1 L Xuri Cellbags. Two passages were expanded at 250 mL volume, followed by one passage at 500 mL volume. CT2 human embryonic stem cell aggregates were passaged using a nickel alloy hexagonal grid slicer with 100 um spacing between the walls. At each passage, sliced aggregates were seeded into a 1 L Xuri Cellbag in mTeSR1 plus 2 to 5 uM Y27632 ROCK inhibitor. The culture conditions consisted of 20 rocks per minute, 4 degree rock angle, 37 degrees C., 5% $CO_2$. The perfusion conditions were designed to remove 15 mL of spent medium from the bioreactor over 50 minutes followed by addition of 15 mL mTeSR1 without Y27632 ROCK inhibitor in 1 minute such that 125 mL was replenished per day using the tubing assembly for gravity settling in non-perfusion bags. A portion of the aggregates were passaged on day 4 or 5 by dissociation with Accutase™ to single cells/small clumps for enumeration. The dissociated cells were enumerated using a Nucleocounter NC200. In passage 1, a total of $1.22 \times 10^{\wedge}8$ viable cells were seeded and $3.12 \times 10^{\wedge}8$ viable cells were recovered with the overall culture at 96.8% viability, representing a 2.6-fold expansion (FIG. 34). In passage 2, a total of $1.15 \times 10^{\wedge}8$ viable cells were seeded and $6.93 \times 10^{\wedge}8$ viable cells were recovered with the overall culture at 91.9% viability, representing a 6-fold expansion. In passage 3, a total of $3.48 \times 10^{\wedge}8$ viable cells were seeded and $1.88 \times 10^{\wedge}9$ viable cells were recovered with the overall culture at 92% viability, representing a 5.4-fold expansion. Over 14 days, there was an overall 83-fold expansion.

Serial Passage: Filter-Less Bag to Filter-Less Bag Passaging with Nickel Alloy Square Grid Slicer In one example, serial passaging of suspension aggregate pluripotent stem cells for three passages was performed. Two passages were expanded at 250 mL volume, followed by one passage at 500 mL volume. CT2 human embryonic stem cell aggregates were passaged using a nickel alloy square grid slicer with 100 um spacing between the walls. At each passage, sliced aggregates were seeded into a Xuri Cellbag in mTeSR1 plus 2 to 5 uM Y27632 ROCK inhibitor. The culture conditions consisted of 20 rocks per minute, 4 degree rock angle, 37 degrees C., 5% $CO_2$. The perfusion conditions were designed to remove 15 mL of spent medium from the bioreactor over 50 minutes followed by addition of 15 mL mTeSR1 without Y27632 ROCK inhibitor in 1 minute such that 125 mL was replenished per day using using the tubing assembly for gravity settling in non-perfusion bags. A portion of the aggregates were passaged on day 5 by dissociation with Accutase™ to single cells/small clumps for enumeration. The dissociated cells were enumerated using a Nucleocounter NC200. In passage 1, a total of $1.14 \times 10^{\wedge}8$ viable cells were seeded and $5.13 \times 10^{\wedge}8$ viable cells were recovered with the overall culture at 97.5% viability, representing a 4.5-fold expansion (FIG. 35). In passage 2, a total of $1.82 \times 10^{\wedge}8$ viable cells were seeded and $1.13 \times 10^{\wedge}9$ viable cells were recovered with the overall culture at 97.4% viability, representing a 6.2-fold expansion. Over 10 days, there was an overall 28-fold expansion.

Serial Passage: Filter-Less Bag to Filter-Less Bag Passaging with Silicon Hexagonal Grid Slicer In one example, serial passaging of suspension aggregate pluripotent stem cells for two passages was performed. Both passages were expanded at 250 mL volume. CT2 human embryonic stem cell aggregates were passaged using a silicon hexagonal grid slicer with 100 um spacing between the walls. At each passage, sliced aggregates were seeded into a 1 L Xuri Cellbag in mTeSR1 plus 2 to 5 uM Y27632 ROCK inhibitor. The culture conditions consisted of 20 rocks per minute, 4 degree rock angle, 37 degrees C., 5% $CO_2$. The perfusion conditions were designed to remove 15-30 mL of spent medium from the bioreactor over 50 minutes followed by addition of 15-30 mL mTeSR1 without Y27632 ROCK inhibitor in 1-2 minutes such that 125 mL was replenished per day using the tubing assembly for gravity settling in non-perfusion bags. A portion of the aggregates were passaged on day 4 or 5 by dissociation with Accutase™ to single cells/small clumps for enumeration. The dissociated cells were enumerated using a Nucleocounter NC200. In passage 1, a total of $5.74 \times 10^{\wedge}7$ viable cells were seeded and $3.15 \times 10^{\wedge}8$ viable cells were recovered with the overall culture at 93.8% viability, representing a 5.5-fold expansion (FIG. 36). In passage 2, a total of $1.95 \times 10^{\wedge}8$ viable cells were seeded and $1.04 \times 10^{\wedge}9$ viable cells were recovered with the overall culture at 97.8% viability, representing a 5.4-fold expansion. Over 9 days, there was an overall 29.4-fold expansion.

Serial Passage: Filter-Less Bag to Filter-Less Bag Passaging with Silicon Hexagonal Grid Slicer and without ROCK Inhibitor In one example, serial passaging of suspension aggregate pluripotent stem cells for two passages was performed. One passages were expanded at 250 mL volume, followed by one passage at 300 mL volume. CT2 human embryonic stem cell aggregates were passaged using a silicon hexagonal grid slicer with 100 um spacing between the walls and coated with a hydrophobic material. At each passage, sliced aggregates were seeded into a 1 L Xuri Cellbag in mTeSR1 without Y27632 ROCK inhibitor. The culture conditions consisted of 20 rocks per minute, 4 degree rock angle, 37 degrees C., 5% $CO_2$. The perfusion conditions were designed to remove 30 mL of spent medium from the bioreactor over 100 minutes followed by addition of 30 mL mTeSR1 without Y27632 ROCK inhibitor in 2 minutes such that half of the medium was replenished per day using the tubing assembly for gravity settling in non-perfusion bags. A portion of the aggregates were passaged on day 4 or 5 by dissociation with Accutase™ to single cells/small clumps. The dissociated cells were enumerated using a Nucleocounter NC200. In passage 1, a total of $4.9 \times 10^7$ viable cells were seeded and $2.9 \times 10^8$ viable cells were recovered with the overall culture at 92.9% viability, representing a 5.9-fold expansion (FIG. 37). In passage 2, a total of $1.45 \times 10^8$ viable cells were seeded and $1.11 \times 10^9$ viable cells were recovered with the overall culture at 98.4% viability, representing a 7.7-fold expansion. Over 9 days, there was an overall 45-fold expansion. The morphology of the aggregates immediately after slicing and after expansion in medium without Y27632 ROCK inhibitor are shown in FIG. 38.

Confirmation of Pluripotency after Serial Passaging

In one example, CT2 cells were maintained as suspension aggregates for five passages on 6 well plates and for three passages in Xuri Cellbags. The expanded cells were analyzed for Oct4, SSEA4 and Tra-1-60 expression by flow cytometry, karyotype and for three germ layer differentiation from embryoid bodies. Cells were fixed in 4% paraformaldehyde and permeabilized in 0.1% Triton X-100, then analyzed by flow cytometry using an Oct4 antibody (BD Pharmingen) conjugated with AlexaFluor 647 and Tra-1-60 antibody (BD Pharmingen) conjugated with R-Phycoerythrin (PE), or with a SSEA4 antibody (BD Pharmingen or Cell Signaling) conjugated with Fluorescein isothiocyanate (FITC). Results as shown in FIG. 8 demonstrate maintenance of pluripotency markers after 5 passages as suspension aggregates on 6 well plates and three serial passages as suspension aggregates in the Xuri Cellbags. FIG. 8 A shows forward scatter and side scatter properties of the cells, FIG. 8 B shows the axis for Oct 4 and Tra-1-60, FIG. 8 C shows Oct4 and Tra-1-60 expression in aggregates expanded for 3 passages in Xuri Cellbags, FIG. 8 D shows staining with isotype antibodies, FIG. 8 E shows the axis for SSEA3, FIG. 8 F shows SSEA3 expression in aggregates expanded for 3 passages in Xuri Cellbags. The data demonstrates maintenance of pluripotency over multiple passages in suspension aggregates maintained under rocking conditions in 6 well plates and in Xuri Cellbags.

CT2 cells expanded for 5 passages as suspension aggregates on 6 well plates and 3 passages as suspension aggregates in Xuri Cellbags demonstrated normal karyotype as shown in FIG. 8. Cells were plated to promote differentiation after forming embryoid body aggregates. The differentiated cells were fixed overnight in 10% Formalin, embedded in paraffin, cut into 5-μm serial sections, and immunohistochemistry (IHC) staining was performed using anti-alpha-fetoprotein (endoderm), anti-smooth muscle actin (mesoderm) and anti-tubulin III (ectoderm). Differentiated cells were stained positive for all antibodies, demonstrating maintenance of pluripotency during serial passage as suspension aggregates after 5 passages on 6 well plates and 3 passages in Xuri Cellbags (FIG. 8 top panel).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for culturing cells in a closed system, the method comprising:
   providing the cells to a culture vessel on a rocking platform bioreactor, wherein the cells are capable of forming cell aggregates in suspension;
   expanding the cells in a culture medium to generate the cell aggregates in suspension;
   performing an automated perfusion of the culture medium, wherein the automated perfusion is performed in absence of a filtration system while retaining the cell aggregates within the culture vessel;
   flowing the cell aggregates across an in-line slicer grid to generate sliced cell aggregates; and
   passaging the sliced cell aggregates in the closed system, wherein the cell aggregates are passed through a mixing device for mixing the cell aggregates prior to flowing the cell aggregates across the in-line slicer grid, and wherein the mixing device is placed between the culture vessel and the in-line slicer grid in the closed system.

2. The method of claim 1, wherein the cells are of plant, animal, insect, or microbial origin.

3. The method of claim 1, wherein the cells comprise pluripotent stem cells or differentiated human cells.

4. The method of claim 1, wherein the cell aggregates are retained within the culture vessel by allowing the cell aggregates to settle by gravity.

5. The method of claim 1, wherein the automated perfusion is performed without human intervention.

6. The method of claim 1, wherein the in-line slicer grid comprises blades that are separated by a distance from about 20 microns to about 500 microns.

7. The method of claim 1, wherein the in-line slicer grid comprises blades that are separated by a distance of about 100 microns.

8. The method of claim 1, wherein the in-line slicer grid is coated with or comprises a hydrophobic material.

9. The method of claim 1, wherein an average diameter of the cell aggregates is no more than 800 microns.

10. A method for culturing cells in a closed system, the method comprising:
    providing the cells in a culture vessel on a rocking platform bioreactor, wherein the cells are capable of forming cell aggregates in suspension;
    expanding the cells in a culture medium to generate the cell aggregates in suspension;
    performing an automated perfusion of the cell culture medium while retaining the cell aggregates within the closed system, wherein the cell aggregates are retained within the closed system by allowing gravity settling of the cell aggregates;
    flowing the cell aggregates across an in-line slicer grid to generate sliced cell aggregates; and
    passaging the sliced cell aggregates in the closed system, wherein the cell aggregates are passed through a mixing device for mixing the cell aggregates prior to flowing the cell aggregates across the in-line slicer grid, and wherein the mixing device is placed between the culture vessel and the in-line slicer grid in the closed system.

11. The method of claim 10, wherein the culture vessel further comprises a tubing assembly comprising a dip tube and a gravity settling chamber.

12. The method of claim 11, wherein the cell aggregates are retained within the gravity settling chamber.

13. The method of claim 10, wherein the automated perfusion is performed in the absence of a filtration system.

14. The method of claim 10, wherein flowing the cell aggregates across the in-line slicer grid is performed at flow rates from about 15 mL/min to about 150 mL/min.

15. The method of claim 10, wherein the in-line slicer grid comprises blades that are separated by a distance from about 20 microns to about 500 microns.

16. The method of claim 15, wherein the in-line slicer grid comprises blades that are separated by a distance of about 100 microns.

17. The method of claim 10, wherein the step of passaging the sliced cell aggregates comprises culturing the sliced cell aggregates in absence of a ROCK inhibitor.

18. The method of claim 17, wherein the sliced cell aggregates comprise pluripotent stem cells.

19. The method of claim 10, wherein an average diameter of the cell aggregates is no more than 800 microns.

20. The method of claim 1, wherein the in-line slicer grid is a polygonal slicer grid.

* * * * *